US006265557B1

(12) United States Patent
Diamond et al.

(10) Patent No.: US 6,265,557 B1
(45) Date of Patent: Jul. 24, 2001

(54) ABO HISTO-BLOOD GROUP O ALLELES OF THE BABOON

(75) Inventors: David Diamond, Duarte; Sandra Nehlsen-Cannarella, Redlands; Omar R. Fagoaga, Colton; Aladar A. Szalay, Highland, all of CA (US)

(73) Assignee: Loma Linda University Medical Center, Loma Linda, CA (US)

( * ) Notice: Subject to any disclaimer, the term of this patent is extended or adjusted under 35 U.S.C. 154(b) by 0 days.

(21) Appl. No.: 08/853,774

(22) Filed: May 9, 1997

(51) Int. Cl.[7] .................... C07H 21/02; C07H 21/04; C12N 15/00
(52) U.S. Cl. ................ 536/23.1; 536/23.2; 536/23.5; 435/320.1
(58) Field of Search .................. 536/23.1, 23.2, 536/23.5; 435/6, 320.1

(56) References Cited

U.S. PATENT DOCUMENTS 5,326,857 * 7/1994 Yamamoto et al. ............. 536/23.2

FOREIGN PATENT DOCUMENTS

WO 91/03484    3/1991   (WO).

OTHER PUBLICATIONS

Buchardt, O. et al., Trends Biotech., vol. 11, pp. 384–386, Aug. 1993.*
Yamamoto, P., et al. (1995) Genomic Organization Of Human Histo–Blood Group ABO Genes. Glycobiology 5:51–58.
Cooper, D.K.C., Ye, Y., Niekrasz, M., Kehoe, M., Martin, M., Neethling, F.A., Kosanke, S., Debault, L.E., Worsley, G., Zuhki, N., Oriol, R., & Romano, E. (1993) Transplantation 56;769–777.
Socha, W.W., & Ruffie, J. (1983) Blood Groups of Primates: Theory, Practice, Evolustionary Meaning, Alan R. Liss, New York, pp 39–51.
Martinko, J.M., Vincek, V., Klein, D. & Klein, J. (1993) Immunogenetics 37:274–278.
Yamamoto, F. (1995) Vox Sang 69:1–7.
Clausen, H., Bennett, E.P., & Grunnet, N. (1994) Transfus-.–Clin.Biol. 2:78–89.
Socha, W.W., Moor–Jankowski, J., Ruffie, J. (1984) J. Med Primatol. 13:11–40.
Bailey, L.L., Nehlsen–Cannarella, S.L., Concepcion, W., & Jolley, W.B. (1985) J. Am. Med. Assoc. 254:3321–3329.
Bailey, L.L., Nehlsen–Cannarella, S.L. (1986) Transplant, Proc. 18:Suppl. 2):88–92.
Yamamoto, F. & Hakomori, S. (1990) J. Biol. Chem. 265:19257–19262.

Bennett, E.P., Steffensen R., Clausen, H., Weghuis, D.O., & van Kessel, A.G. (1995) Biochem. Biophys. Res. Comm. 206:318–325.
Kominato, Y., McNeill, Ph.D., Yamamoto, M., Russel, M., Hakomori, S. & Yamamoto, F. (1992) Biochem. Biophys. Res. Comm. 189:154–164.
Yamamoto, F., Clausen, H., White, T., Marken, J. & Hakomori, S. (1990) Nature 345:229–233.
Yamamoto, F., McNeill, P.D., Yamamoto, M., Hakomori, S., Bromilow, I.M., Duguid, J.K.M. (1993) Vox Sang 64:175–178.
Grunnet, N., Steffensen, R., Bennett, E.P. & Clausen, H. (1994) Vox Sang 67:210–215.
Nehlsen–Cannarella, S.L. & John, M. (1987) Immunological Investigations 16:57–62.
Yamamoto, F., McNeill, P.D., Yamamoto, M., Hakomori, S. & Harris, T. (1993) Vox Sang 64:171–174.
Perry–O'Keffe, H., Yao, X.–W., Coull, J.M., Fuchs, M., & Fuchs, M., & Egholm, M. (1996) Proc. Nat. Acad. Sci, USA. 93: 14670–14675.
Diamond et al., Sequence Comparison of Baboon ABO Histo–Blood Group Alleles: Lesions Found in O Alleles Differ between Human and Baboon, Blood Cells, Molecules, and Diseases (1997) 23:242–251.
Doxiadis et al., Characterization of the ABO blood group genes in macaques: evidence for convergent evolution, Tissue Antigens (1998) 51:321–326.
Ogasawara et al., Extensive polymorphisms of ABO blood group gene: three major lineages of the alleles for the common ABO phenotypes, Hum Genet (1996) 97:777–783.
Saitou et al., Evolution of Primate ABO group blood group genes and their homologous genes, Mol. Biol. Evol. 14:399–411(1997).
Socha et al., Red Cell Polymorphisms in nonhuman primates: A Review, J. Med. Primatol. 24:282–305 (1995).

* cited by examiner

Primary Examiner—Ponnathapu Achutamurthy
Assistant Examiner—Peter P. Tung
(74) Attorney, Agent, or Firm—Knobbe, Martens, Olson & Bear, LLP

(57) ABSTRACT

This invention relates to histo-blood group O alleles of baboon. The major O allele retains identifying sequence characteristics of the baboon A allele. Other alleles, including a B-like allele, are also disclosed herein. The O alleles of baboon are closer in sequence similarity to the baboon A and B alleles than are any of the baboon ABO alleles to the human alleles of the ABO locus. This invention also provides materials and methods for identifying O alleles, and carriers of O alleles, as well as methods for producing baboons and baboon cells, tissues, and organs having a group O phenotype. Group O baboons, cells, tissues, and organs of the invention are useful for xenotransplantation.

2 Claims, 5 Drawing Sheets

FIG. 1

| FIG. 1A |
|---|
| FIG. 1B |
| FIG. 1C |
| FIG. 1D |

FIG. 1A

```
                                                                                                    △
HumA     ---  ---  ---  ---  --T  ---  ---  ---  --C  --G  ---  ---  ---  ---  ---  ---  ---  ---  282
O (bab 5) --- --- --- --- --- --- --- --- --- --- --- --- --- --- --- --- --- ---
a (bab 9) T AGG AAG GAC GTC CTT GTC ACC GTG CCT TGG CTG GCT CCC ATT
B (bab 7) --- --- --- --- --- --- --- --- --- --- --- --- --- --- ---

HumA     ---  ---  ---  --A  ---  ---  ---  ---  ---  ---  ---  ---  ---  ---  ---  ---  ---  ---  327
O (bab 5) --- --- --- --- --- --- --- --- --- --- --- --- --- --- --- --- --- ---
A (bab 9) GTC TGG GAG GGC ACG TTC AAC ATC GAC CTC AAC GAG CAG TTC
B (bab 7) --- --- --- --- --- --- --- --- --- --- --- --- --- --- ---

HumA     ---  ---  ---  ---  ---  ---  ---  ---  ---  --T  ---  ---  ---  ---  ---  ---  --G  372
O (bab 5) --- --- --- --- --- --- --- --- --- --- --- --- --- --- --- --- --- ---
A (bab 9) AGG CTC CAG AAC ACC ACC ATC GGG TTA ACT GTG TTT GCC ATC AAA
B (bab 7) --- --- --- --- --- --- --- --- --- --- --- --- --- --- ---

<--exon 6 | exon 7-->
HumA     ---  ---  --T  ---  ---  ---  ---  ---  ---  ---  ---  ---  ---  ---  ---  ---  ---  ---  417
O (bab 5) --- --- --- --- --- --- --- --- --- --- --- --- --- --- --- --- --- ---
A (bab 9) AAA TAC GTG GCC TTC CTG AAG CTG TTC TTC GAG ACG GCG GAG AAG
B (bab 7) --- --- --- --- --- --- --- --- --- --- --- --- --- --- ---
```

```
HumA       --- --- --- --- --- --- --- --- --- --- --- --- --- --- ---  912
O (bab 5)  --- --- --- --- --- --- --- --- --- --- --- --- --- --- ---
A (bab 9)  GTC GAC CAG GCC AAC GGC ATC GAG GCC GTG TGG CAC GAC GAG AGC
B (bab 7)  --- --- --- --- --- --- --- --- --- --- --- --- --- --- ---

HumA       --- --- --- --- --- --- --- --- --- --- --- --- --- --- ---  957
O (bab 5)  --- --- --- --- --- --- --- --- --- --- --- --- --- --- ---
A (bab 9)  CAC CTG AAC AAG TAC CTG CTG CGC CAC AAA CCC ACC AAG GTG CTC
B (bab 7)  --- --- --- --- --- --- --- --- --- --- --- --- --- --- ---

HumA       --- --- --- T-- --- --- --- --- --- --- --- --- --- --C 1002
O (bab 5)  --- --- --- --- --- --- --- --- --- --- --- --- --- ---
A (bab 9)  TCC CCC GAG TGG TGG CTG GAC CAG CAG CTG CTG GGC TGG CCT GCG
B (bab 7)  --- --- --- --- --- --- --- --- --- --- --- --- --- --- ---

HumA       --- --- --- --- --- A-T --- --- --- --- --- --- --- --- --- 1047
O (bab 5)  --- --- --- --- --- --- --- --- --- --- --- --- --- --- ---
A (bab 9)  GTC CTG AGG AAG CTG TTC GCG GCG GTG CCC AAG AAC CAC CAG
B (bab 7)  --- --- --- --- --- A-G --- --- --- --- --- --- --- --- ---
                               *

HumA       --- --G --- --- --- 1065
O (bab 5)  --- --G --- --- ---
A (bab 9)  GCG GTC CGT AAC CCG TGA
B (bab 7)  --- --G --- --- ---
```

ABO HISTO-BLOOD GROUP O ALLELES OF
THE BABOON

BACKGROUND OF THE INVENTION

The transplantation of organs to patients having organ diseases or defects was at first limited by technical obstacles to transplantation surgery, and later by the lack of effective immunosuppressive agents. As many of these obstacles were overcome, the major limiting factor quickly became the scarcity of suitable donor organs. While public information campaigns have made headway in convincing people of the importance of designating themselves as potential organ donors, there is still a severe shortage of organs for transplantation. Many patients can only wait as their condition worsens, uncertain of whether a suitable organ will become available before they are too ill to benefit from a transplant.

An obvious limit on the number of vital organs for transplantation is the fact that such organs only become available under unusual circumstances: the death of an otherwise relatively healthy person in a manner that does not damage the vital organs. Therefore, vital organs for human allotransplantation (transplantation between individuals of the same species) will likely always be in short supply. Accordingly, xenotransplantation (transplantation between individuals of different species) provides a desirable additional source of organs for transplantation to humans.

In the development of an optimal xenotransplantation system, several factors must be considered. First, a close phylogenetic relationship between the donor and the recipient is preferable to a more distant relationship. For example, for xenotransplantation of a vital organ to a human, a non-primate generally would be a less desirable donor, in terms of phylogenetic relationship, than a primate.

The order Primates is divided into two suborders: the prosimians and the anthropoids. The anthropoids are further divided into two infraorders: the Platyrrhini, or new world monkeys, and the Catarrhini. The Catarrhini are likewise divided into two superfamilies: the old world monkeys and the hominoids. Hominoids include the great apes and humans. According to this classification scheme, the old world monkeys are more closely related to humans than are the prosimians or the new world monkeys, but not as closely related to humans as are the four genera of apes: Hylobates (gibbons), Pongo (orangutans), Gorilla, and Pan (chimpanzees).

A second very important factor in selecting a preferred xeno-species is its amenability to human handling, captive breeding, experimentation, and the like. Generally speaking, old world monkeys are much more easily maintained than are the apes.

Other important factors for an optimal xenotransplant source species include reproductive rate, body size, cost of maintenance, and anatomic and physiologic similarity to humans. The reproductive rate is a function of the average age at which individuals of the species reach sexual maturity, as well as the gestational duration, multiplicity of births, and number of reproductive years. The size of the source species is important because organs that are too small are not always suitable for transplantation into humans. Since baboons, (genus Papio) are the largest of the old world monkeys, and since their anatomic and physiologic characteristics are very similar to those of humans, they represent a desirable combination of the most important factors.

Baboons do, however, present shortcomings of their own as a genuine alternative to allotransplantation. They do not reach sexual maturity until about age 4 or 5, they typically deliver only one offspring per gestation, and they present a potential risk of transmitting erstwhile baboon pathogens to humans. All of these facts make baboons very unlike the familiar laboratory and model system animals that can be multiplied virtually at will, and that are hosts to pathogens that are relatively well known and easily controlled. For all of these reasons, creating a large colony of baboons to provide a significant supply of donor organs would be a slow and very costly process.

An even greater obstacle to the development of baboons as a useful xenotransplantation source species is that, while the most common human histo-blood group is O, baboons of group O are exceedingly rare. The resulting incompatibility of the organs of virtually all baboons with members of the largest human blood group, as discussed in greater detail below, significantly reduces the utility of present captive baboon colonies, as well as almost all baboons in the wild, as good sources of xenotransplant organs for humans as a group.

Therefore, in addition to the scarcity of suitable donor organs, compatibility considerations further limit the potential pool of donors for a particular patient. This is equally true for both allo- and xeno-organ sources.

Incompatible organs are very likely to be rejected. For example, when organs are transplanted across the ABO histo-blood group barrier, there is a high incidence of antibody-mediated rejection. One antibody-mediated form of organ rejection, known as hyperacute vascular rejection, may be quite rapid. In heart and kidney transplants, hyperacute vascular rejection has been estimated to occur in approximately 66% of ABO-mismatched cases. A second type of antibody-mediated rejection is known as accelerated rejection. In some cases of accelerated rejection, an organ recipient generates anti-donor antibodies which may then aberrantly cross react with the recipient's own cells leading, for example, to complications or death brought on by agglutination of the recipient's blood cells arising from his or her own antibodies. In addition to antibody-mediated rejection in its various manifestations, cellular rejection, associated with the cellular immune response, may also occur, albeit more slowly. Cellular rejection may be a risk even in cases where antibody-mediated rejection has been avoided or overcome. Cooper, D. K. C., Ye, Y., Niekrasz, M., Kehoe, M., Martin, M., Neethling, F. A., Kosanke, S., DeBault, L. E., Worsley, G., Zuhki, N., Oriol, R., & Romano, E. (1993) Transplantation 56:769–777 (hereinafter Cooper et al. (1993)).

Several approaches have been proposed to reduce antibody-mediated rejection, some of which may also diminish the extent of cellular rejection. A splenectomy may be performed, and may accompany pre-transplant plasmapheresis, a process that temporarily removes antibodies from the blood. However, both splenectomy and plasmapheresis may nonspecifically depress all immune responses, instead of exclusively blocking the response to ABO incompatibility alone. Cooper et al. (1993).

A more specific approach to A/B antibody removal involves passage of a patient's plasma through an affinity column that displays the specific glycans recognized by anti-A and/or anti-B antibodies. Only A/B antibodies are bound to the column while non-A/B antibodies remain in the plasma as it passes through the column. Another alternative is to competitively occupy the A/B antibodies without removing them from the plasma, by intravenously infusing small carbohydrates to which the antibodies specifically bind, thus selectively inactivating the antibodies that could otherwise mount an undesirable response to the transplanted organ. Of course, any of the above therapies may also be combined with administration of immunosuppressive drugs. Nevertheless, since A/B antibodies develop and are maintained via continuous sensitization by microbial flora in the gastrointestinal tract, the temporary removal or inactivation of A/B antibodies provides no long-term solution. Cooper et al. (1993).

Incompatibility at the histo-blood ABO locus is therefore a major determinant in limiting the suitability of a xeno- or allo-donor organ for a particular recipient. Commonly known to control a person's blood-group, the products of the ABO locus not only affect antigens on erythrocytes, but also on many other cell surfaces, including the epithelium of several important organs. Therefore, if a donor and recipient are not compatible for traditional blood transfusion because of ABO phenotype differences, they will be likewise incompatible for organ transplantation.

The ABO histo-blood group antigens, the basis of blood group, are found in all anthropoid primates. Socha, W. W., & Ruffié, J. (1983) *Blood Groups of Primates: Theory Practice, Evolutionary Meaning* Alan R. Liss, New York. These antigens, which are terminal carbohydrate structures, can be found both in soluble form and on the surface of a variety of tissues, depending on the species examined. Additionally, antibodies to the non-expressed antigen(s) are universally present, agglutinating mismatched blood and facilitating complement-mediated attack on tissues following transplant. Genetically, the phenotype is controlled by a single locus that can be occupied by three fundamental alleles encoding enzymes with either A or B activity or no activity (group O).

The A and B enzymes are both glycosyltransferases. The enzymes each transfer a different sugar residue to the same core oligosaccharide. The core oligosaccharide may be variable in length, but terminates with a disaccharide of D-galactose (D-Gal) and N-acetyl-D-glucosamine (GlcNAc), which is usually modified to replace the GlcNAc with a residue of L-fucose (L-Fuc). The enzyme product of the A allele, A transferase, specifically catalyzes the transfer of N-acetyl-D-galactosamine (GalNAc) to the core D-Gal, resulting in a branched terminal trisaccharide having both GalNAc and L-Fuc attached to the core D-Gal. This trisaccharide is the A antigen, and is bound by A antibodies. Likewise, the B allele product, B transferase, specifically transfers D-Gal to the same core oligosaccharide. The resulting trisaccharide, the B antigen, has both L-Fuc and D-Gal attached to the core D-Gal.

The human O allele specifies no active enzyme, and the recessive O phenotype occurs in the absence of any active A or B transferase. The oligosaccharide therefore terminates with a D-Gal/L-Fuc disaccharide. This disaccharide structure is known as the H antigen, and is not bound by either A or B antibodies. In the rare Bombay phenotype, the original GlcNAc of the core disaccharide is never replaced by L-Fuc, and so the core disaccharide retains the D-Gal/GlcNAc terminal structure.

Cells with A transferase activity display the A glycan, while cells with B transferase activity instead display the B glycan. Cells with both activities have both types of glycan antigen modifications, and cells with neither A nor B transferase display the H antigen. The A and B antibodies specifically recognize the A and B glycans, respectively. Martinko, J. M., Vincek, V., Klein, D. & Klein, J. (1993) *Immunogenetics* 37:274–278; see also Yamamoto, F. (1995) *Vox Sang* 69:1–7 (hereinafter Yamamoto (1995)); and Clausen, H., Bennett, E. P., & Grunnet, N. (1994) *Transfus.-Clin.Biol.* 2:78–89.

Since cells from histo-blood group O individuals lack both antigens, they are not subject to attack by A/B antibodies, and therefore can be freely transplanted. Thus, blood group O individuals are considered universal donors of both blood and organs. However while blood group O is the most common group in humans, it is very rare in baboons. Socha, W. W., Moor-Jankowski, J., Ruffié, J. (1984) *J. Med Primatol.* 13:11–40. This has been an impediment to the development of xenotransplantation protocols involving the use of baboon organs. Bailey, L. L., Nehlsen-Cannarella, S.L., Concepcion, W., & Jolley, W. B. (1985) *J. Am. Med. Assoc.* 254:3321–3329; Bailey, L. L. & Nehlsen-Cannarella, S.L. (1986) *Transplant. Proc.* 18(Suppl. 2):88–92.

Previous work on the molecular genetics of the ABO system has established the cDNA sequence and genomic structure of the locus in humans, as well as the amino acid residues conferring the different enzymatic activities. Yamamoto, F. & Hakomori, S. (1990) *J. Biol. Chem.* 265:19257–19262); Yamamoto (1995); Bennett, E. P., Steffensen, R., Clausen, H., Weghuis, D. O., & van Kessel, A. G. (1995) *Biochem. Biophys. Res. Comm.* 206:318–325; Yamamoto, F., McNeill, P. D., & Hakomori, S. (1995) *Glycobiol.* 5:51–58. The coding sequence of the transferase is divided into seven exons. Exon 6 and 7 encode the bulk of the enzyme (13% and 65%, respectively), including its active site. In all examined primate species the residues critical for determining donor substrate specificity (i.e., A versus B activity) are found at amino acid positions 266 and 268, Leu vs. Met and Gly vs. Ala, respectively. Martinko et al. (1993); Kominato, Y., McNeill, P. D., Yamamoto, M., Russel, M., Hakomori, S. & Yamamoto, F. (1992) *Biochem. Biophys. Res. Comm.* 189:154–164 (amino acid position numbering is according to Yamamoto (1995) and Clausen, et al. (1994)).

In humans, blood group O arises from either of two mutations in an A-like background: a frameshift in exon 6 leading to premature termination, or a Gly>Arg mutation in exon 7 at position 268. Yamamoto, F., Clausen, H., White, T., Marken, J. & Hakomori, S. (1990) Nature 345:229–233 (hereinafter Yamamoto et al. (1990)); Yamamoto, F., McNeill, P. D., Yamamoto, M., Hakomori, S., Bromilow, I. M., Duguid, J. K. M. (1993) *Vox Sang* 64:175–178; Grunnet, N., Steffensen, R., Bennett, E. P. & Clausen, H. (1994) *Vox Sang* 67:210–215. However, prior to the work disclosed herein, the nature of the allele(s) conferring an O phenotype in baboons was not known.

Because organs of O phenotype baboons would not elicit an ABO-induced rejection, and because of the other advantageous features of baboons as a xenotransplant source species for man, a group O strain of baboons would be of great medical importance. However, since group O baboons are so rare, the process of locating naturally occurring founders for such a strain would be difficult. Moreover, even if it were possible to locate some few group O baboons of both sexes, it would still take many years of breeding to achieve a group O colony of significant size, because of the relatively slow reproduction and maturation of baboons.

Random mating of non-O individuals, and subsequent postnatal screening of offspring to identify those of O phenotype is equally impractical. Given the rarity of the group O phenotype, it may be assumed that the O allele is also relatively rare, unless A/O or B/O heterozygotes are somehow selected for. The following hypothetical model illustrates the impracticality of random breeding and postnatal selection of O homozygotes:

Assuming no selection and random mating, if the frequency of the O phenotype in a population of baboons is 1%, it would be expected that the frequency of the O allele in that population's gene pool is 10%. Assuming that the A and B alleles are of equal frequency (45% each), random mating would be expected to produce the following genotype frequencies

A/A=0.2025 B/B=0.2025
A/O=0.09 B/O=0.09
A/B =0.405 O/O=0.01 resulting in the following phenotypic frequencies

A=0.2925
B=0.2925
AB=0.405
O=0.01

If the A and B (but not AB) individuals in this population were randomly mated, the frequencies of the alleles in the A and B breeding pool would be p(A)=0.423
q(B)=0.423
r(O)=0.154 and 100 such matings would on average produce only 2 group O offspring [$(0.154)^2*100=2.37$].

Using the same Hardy-Weinberg model, if the O allele were assumed to be as frequent as 30%, rather than 10%, the O individuals resulting from random mating and no selection would be 9% of the population, and 100 matings of phenotype A and/or B individuals would be expected to produce 10 group O offspring. It is well documented that the O phenotype is rare in baboons. Given the rarity of the O phenotype, it seems doubtful that the frequency of the O allele is as great as 30%.

Regardless of the actual allele frequency, the above exercise demonstrates that conventional breeding involving matings of non-O individuals can make, at best, incremental progress toward the establishment of a stock of group O baboons. Accordingly, there is a need for a prenatal, or even pre-mating, selection that identifies and favors the O alleles and enhances the rate of production of group O offspring. The invention disclosed herein provides a way to greatly accelerate the establishment of a group O strain of baboon for medical use.

SUMMARY OF THE INVENTION

The present invention provides histo-blood group O alleles of baboon. The isolated polynucleotides corresponding to the O allele may have sequence determinants characteristic of the baboon A allele, such as, for example, $T_{796}$, $G_{803}$, and $A_{813}$. For references in the description and in the claims to specific nucleotide positions such as, for example, $T_{796}$, $G_{803}$, $A_{813}$, $A_{796}$, $C_{803}$, $G_{813}$, $N_{629}$, $N_{651}$, $N_{704}$, $N_{711}$, $N_{796}$, $N_{803}$, and $N_{813}$, and the like, the nucleotide position in subscript numbers refers to the position of the nucleotide as it corresponds to the sequence of the Human A allele as shown in FIG. 1. One embodiment of this aspect of the invention is an O allele having the sequence of SEQ ID NO:2. In an alternative embodiment of this aspect of the invention, the O allele may have sequence determinants corresponding to the baboon B allele, such as, for example, $A_{796}$, $C_{803}$, and $G_{813}$. Another embodiment of this aspect of the invention is a recombinant construct having all or part of the sequence of a baboon O allele.

A second aspect of the invention provides an isolated polynucleotide specific to a region of at least 12 contiguous nucleotides of a baboon histo-blood group O allele, wherein the contiguous nucleotides encompass a mutation in a baboon histo-blood group A or B allele. The isolated polynucleotide of this aspect of the invention may be capable of hybridizing to the contiguous nucleotides at 37° C. in 6×SSC, 0.1% SDS, or higher stringency. In one embodiment, the isolated polynucleotide may have a sequence complementary to all of the contiguous nucleotides. Alternatively, the isolated polynucleotide may have a sequence wherein at least one nucleotide of the polynucleotide is non-complementary to at least one nucleotide of the contiguous nucleotides. The isolated polynucleotide of this aspect of the invention may be a peptide nucleic acid. In one embodiment, the isolated polynucleotide may have sequence determinants characteristic of the baboon A allele, such as, for example, nucleotides $T_{796}$, G803, and $A_{813}$. In some embodiments, the polynucleotide may have a sequence of at least 12 nucleotides corresponding to or complementary to one or more of SEQ ID NO:5, SEQ ID NO:15, SEQ ID NO:17, SEQ ID NO:20 and SEQ ID NO:22. In an alternative embodiment of this aspect of the invention, the isolated polynucleotide may have sequence determinants of the baboon B allele, such as, for example, $A_{796}$, $C_{803}$, and $G_{813}$. In some embodiments, the polynucleotide may have a sequence of at least 12 nucleotides corresponding to or complementary to one or more of SEQ ID NO:16, SEQ ID NO:18, and SEQ ID NO:19. Another embodiment of this aspect of the invention provides a recombinant construct having the isolated polynucleotide sequence of this aspect of the invention together with a vector.

An additional aspect of the invention is a method of producing a group O non-human primate. The steps of the method include: evaluating a plurality of non-human primates for presence in any of the primates of an O allele; providing a male non-human primate and a female non-human primate, each of the primates being determined to carry at least one allele of histo-blood group O; crossing gametes of the male with the female; and selecting a progeny of the crossing step, the progeny having two alleles of histo-blood group O. In some embodiments, the method has the additional steps of: identifying at least one individual of histo-blood group phenotype A or B from the plurality of non-human primates, and screening a nucleic acid sample of the individual for presence of a sequence determinant discordant with the phenotype. This method includes embodiments wherein the phenotype is A and the sequence determinant is at least one of nucleotides $A_{796}$, $C_{803}$, and G813, which correspond to the B allele. Alternatively, the phenotype may be B and the sequence determinant may be at least one of nucleotides $T_{796}$, G803, and $A_{813}$, corresponding to the A allele. The sequence determinants in this method may be detected by a polynucleotide probe specific to a region of at least 12 contiguous nucleotides of a baboon ABO histo-blood group allele, wherein the contiguous nucleotides encompass a mutation in a baboon histo-blood group A or B allele, and the isolated polynucleotide is capable of hybridizing to the contiguous nucleotides at 37° C. in 6×SSC, 0.1% SDS, or higher stringency.

In another embodiment of this aspect of the invention, an O allele is identified by detecting in nucleic acids of the primates or the progeny at least one nucleotide difference between the O allele and an A or B histo-blood group allele. The method includes embodiments wherein the nucleotide difference is detected by mobility of a polynucleotide in a chromatographic or electrophoretic system, or by activity of an ABO allele-specific restriction endonuclease. In other embodiments, the nucleotide difference is detected by a polynucleotide probe specific to a region of at least 12 contiguous nucleotides of a baboon ABO histo-blood group allele, with the contiguous nucleotides encompassing a mutation in a baboon histo-blood group A or B allele, and the isolated polynucleotide being capable of hybridizing to the contiguous nucleotides at 37° C. in 6×SSC, 0.1% SDS, or higher stringency. In one embodiment, the polynucleotide probe may include a peptide nucleic acid. The polynucleotide probe of this aspect of the invention may have a sequence complementary to all of the contiguous nucleotides, or the probe may have a sequence wherein one nucleotide of the polynucleotide is non-complementary to at least one nucleotide of the contiguous nucleotides. In another embodiment of this aspect of the invention, the nucleotide difference is detected by a mismatch detection activity that is active at a position of mismatch between the polynucleotide probe and the region of contiguous nucleotides of the baboon histo-blood group allele sequence. The mismatch detection activity may include, for example, a mismatch cleavage activity, a polynucleotide extension activity, or a ligation activity.

The crossing step of the method of this aspect of the invention may be performed in vitro. The selecting step may be performed during an embryonic developmental stage of the progeny. This aspect of the invention also contemplates a group O non-human primate produced by the disclosed method. It likewise contemplates a group O cell or cell culture, and a group O tissue, including, for example, blood or semen, from the group O non-human primate produced by the method. Also within the scope of this aspect of the invention is a group O embryo or organ from the group O non-human primate of the invention. Further, the method may be used to produce a group O strain of non-human primate. The strain may be produced by crossing a group O non-human primate of the invention with a non-human primate having at least one O allele. A further embodiment of the method is a group O individual of the strain thus produced.

Another aspect of the invention provides a method of genetically modifying a cell of a non-human primate to produce a cell having a histo-blood group O phenotype. The method includes the steps of: providing a target cell sample of a non-human primate; transfecting the sample with a recombinant construct having at least 12 contiguous nucleotides corresponding to a sequence of an ABO locus, the locus having a promoter region and a coding region; and modifying the phenotype of the cell by the action of the recombinant construct. In this method the contiguous nucleotides may be fully complementary to the sequence of the ABO locus. Alternatively, the contiguous nucleotides may include one mismatch with the sequence of the ABO locus. In another embodiment, the contiguous nucleotides may have six or fewer mismatches with the sequence of the ABO locus. The method of this aspect of the invention may include the additional step of growing the cell. The growing step may involve culturing the cell in a cell culture, and/or propagating the cell. The cell or cells of this aspect of the invention may be, for example, zygotic cells, embryonic cells, or fetal cells, and the growing step may include gestating the cell or cells.

In some embodiments of this aspect of the invention, the construct may be an antisense construct. The construct may also be a DNA/RNA chimera. The action of the construct may be homologous recombination, or it may include cleavage of an RNA sequence by a ribozyme. In the method, the cell sample may include, for example, at least one zygotic, embryonic, fetal or gonadal cell. The method may be practiced to produce a group O strain of non-human primate. Likewise, the method may be used to produce a genetically modified individual of histo-blood group O. Also contemplated within this aspect of the invention are a group O cell, cell culture, or tissue, including, for example, blood or semen, from the group O individual produced by the method. Further embodiments include a group O embryo and a group O organ from the group O individual.

In another aspect of the invention, there is provided a kit for detecting an allele of histo-blood group O. The kit may be adapted to detect at least one nucleotide difference between the O allele and an A or B histo-blood group allele. The kit may have indicia for manifesting the presence of the O allele. The kit may also include a peptide nucleic acid. In another embodiment, the kit may include an isolated polynucleotide having a sequence corresponding to or complementary to at least one of SEQ ID NO:5, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. The kit may also include an ABO allele-specific restriction endonuclease.

An additional aspect of the invention is a method of screening a baboon to determine whether the baboon is a carrier of a histo-blood group O allele. This method includes the steps of: providing a nucleic acid sample from the baboon; contacting the nucleic acid sample with a polynucleotide specific to a region of at least 12 contiguous nucleotides of a baboon histo-blood group allele, the contiguous nucleotides encompassing a mutation in a baboon histo-blood group A or B allele, or at least one of the nucleotide positions $N_{796}$, $N_{803}$, and $N_{813}$, wherein the polynucleotide is capable of hybridizing to the contiguous nucleotides at 37° C. in 6×SSC, 0.1% SDS, or higher stringency. Another step of this method includes determining whether the baboon is a carrier of a histo-blood group O allele based on hybridization between the polynucleotide and the nucleic acid sample. In this method the polynucleotide may have at least one of the nucleotide positions selected from the group consisting of $N_{629}$, $N_{651}$, $N_{704}$, $N_{711}$, $N_{796}$, $N_{803}$, and $N_{813}$. The hybridization in this method may be a complete hybridization between the between the nucleic acid sample and the polynucleotide, or it may include a single nucleotide mismatch between the nucleic acid sample and the polynucleotide. Alternatively, the hybridization may include a mismatch of at least two nucleotides between the nucleic acid sample and the polynucleotide.

BRIEF DESCRIPTION OF THE DRAWINGS

FIG. 1 is a sequence comparison showing the sequences of exon 6 and exon 7, through the termination codon, of representative homozygous baboons of each blood group, aligned with the published sequence for human A transferase.

DETAILED DESCRIPTION OF THE INVENTION

Figure 2:
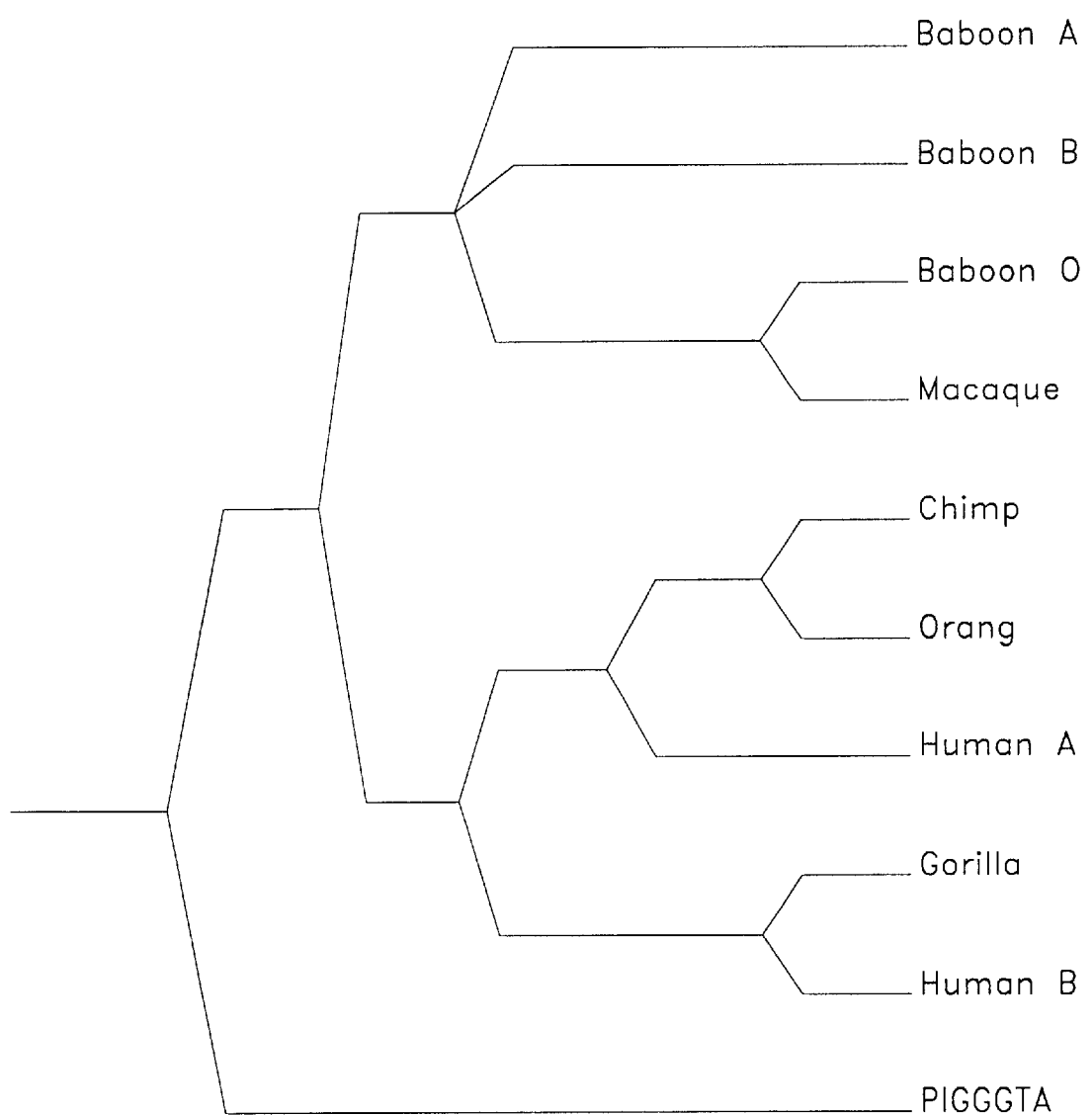
FIG. 2 is a cladogram for the ABO transferase locus, wherein A-type activity would be predicted for the chimpanzee, orangutan, and macaque sequences, and B-type activity would be predicted for the gorilla sequence; PIGGGTA, the related α-1,3-galactosyltransferase of *Sus scrofa*, was used as an outgroup.

The present invention provides a solution to a chief difficulty in using baboons for xenotransplantation of organs and other tissues. With the isolated polynucleotides and methods disclosed herein, heterozygote carriers of O alleles may be identified prior to breeding, and embryos homozygous for O alleles can be selected prior to gestation. Accordingly, rather than a conventional breeding program that may incrementally increase the number of O phenotype offspring of non-O parents, the present invention provides a way to approach 100% production of O individuals from matings of selected non-O animals. This invention therefore dramatically changes the rate and efficiency with which a line of group O baboons may be established for use as universal xeno-donors of organs and other tissues. The methods of the invention may also be used to produce group O strains of other non-human primates.

This invention discloses the sequences of multiple baboon O alleles. These alleles are distinct from previously disclosed sequences of A and B alleles of baboons and of humans. They are also distinct from previously published sequences of human O alleles.

It is understood that an individual possessing two O alleles, and thus lacking any allele of either A or B, will be phenotypically group O. This is true if the individual possesses identical O alleles and is also the case where the two O alleles in the individual's genome are different from each other. Since it is conventional to designate individuals having two O alleles as being homozygous, this disclosure may refer generally to O phenotype individuals as homozygotes, or as being homozygous, even where the two O alleles of the individual are distinct forms of O. This same convention may also be applied herein to individuals having two A alleles or two B alleles, regardless of whether the alleles are strictly identical.

Using immunofluorescent serologic phenotyping of buccal epithelium (Nehlsen-Cannarella, S. L. & Bohn, M. (1987) *Immunological Investigations* 16:57–62), we discovered an O histo-blood group baboon (Papio cynocephalus anubis). With this finding, and to aid our work using baboons, whether as a model system or as potential organ donors to humans, we examined the molecular basis of blood group O in baboons. We discovered the existence of at least two prototype O alleles in baboon: one, now observed in two O homozygotes and several apparent B/O heterozygotes, is derived from an A allele; another, observed in an apparent A/O heterozygote, is derived from a B allele. A possible third prototype O allele, A-derived, has also been observed in a pair of B/O heterozygotes. None of these baboon O alleles shares the mutations found in the human O alleles.

Histo-blood group O has only rarely been observed in baboons. Recent discovery of such a group O baboon has provided us the opportunity to investigate the molecular genetics of the ABO locus in baboons and compare its alleles to those from other primates. Phylogenetic analysis suggests that the ape and old world monkey lineages diverged prior to the divergence of the A and B transferases and that their existence in both lineages is an example of parallel evolution. The major baboon prototype O allele, observed in two homozygous and several heterozygous animals in our study, is related to the A allele as it is in humans, although the mutations in the baboon A allele that resulted in the baboon O allele are distinct from the mutations in the human A allele that led to the human O alleles. Likewise, the defects found in the two known human O alleles have not been observed in any of the baboon O alleles. This disclosure provides phylogenetic analysis in support of the fact that the baboon and human O alleles originated as different evolutionary events, and are not merely simple variants of each other.

Determination of ABO blood group phenotype in baboons can be done either by forward or reverse typing. Reverse typing characterizes the ABO phenotype by the absence of the corresponding antibody in the serum. Forward typing directly detects the presence of A and/or B antigens on the surface of cells. Unlike hominoids (humans and great apes), old world monkeys such as the baboon do not express ABO antigens on erythrocytes. However, the antigens are expressed on the cells of other tissues, including epithelial cells. Thus while conventional reverse typing is feasible in baboons, forward typing was performed on scrapings of buccal epithelium, rather than on erythrocytes as is typically done in humans. Both forward and reverse typings were performed to determine the ABO blood group of all baboons studied (Table 1). Generally this phenotyping was consistent with subsequent genotyping (below).

TABLE 1

| Baboon | N480 | N629 | N651 | N704 | N711 | N1024 | Phenotype | Sequence Type | Genotype |
|---|---|---|---|---|---|---|---|---|---|
| 9 | G | C | C | C | C | G | A | AA | AA |
| 10 | G | C | C | C | C | G/A | A | AA | AA |
| 31 | G | C | C | C | C | G | A | AA | AA |
| 7 | G | C | C | C | C | A | B | BB | BB |
| 11 | A/G | C | C | C | C | G/A | B | BB | BB |
| 12 | G | C | C | C | C | G/A | B | BB | BB |
| 13 | A/G | C | C | C | C | G/A | B | BB | BB |
| 15 | G | C | C | C | C | G/A | B | BB | BB |
| 17 | G | C | C | C | C | G/A | B | BB | BB |
| 19 | A/G | C | C | C | C | G/A | B | BB | BB |
| 20 | G | C | C | C | C | A | B | BB | BB |
| 22 | G | C | C | C | C | G/A | B | BB | BB |
| 23 | A/G | C | C | C | C | G | B | BB | BB |
| 24 | G | C | C | C | C | G/A | B | BB | BB |
| 26 | G | C | C | C | C | G | B | BB | BB |
| 27 | G | C | C | C | C | A | B | BB | BB |
| 28 | G | C | C | C | C | G/A | B | BB | BB |
| 29 | G | C | C | C | C | A | B | BB | BB |
| 33 | G | C | C | C | C | G/A | AB | AB | AB |
| 30 | A/G | C | C | C | C | G/A | A | AB! | A0 |
| 3 | G | C | C | C | C | A | B | AB | B0 |
| 16 | G | C | C | C | C | G/A | B | AB | B0 |
| 1 | A/G | T/C | T/C | G/C | T/C | G/A | A | AA | A0? |
| 2 | A/G | T/C | T/C | G/C | T/C | G/A | A | AA | A0? |

TABLE 1-continued

| Baboon | N480 | N629 | N651 | N704 | N711 | N1024 | Phenotype | Sequence Type | Genotype |
|---|---|---|---|---|---|---|---|---|---|
| 6 | A/G | T/C | T/C | G/C | T/C | G/A | B | AB | B0 |
| 8 | A/G | T/C | T/C | G/C | T/C | G/A | B | AB | B0 |
| 14 | A/G | T/C | T/C | G/C | T/C | G | B | AB | B0 |
| 21 | A/G | T/C | T/C | G/C | T/C | G | B | AB | B0 |
| 18 | A/G | T/C | T/C | G | T | G | B | AB | B0 |
| 5 | A | T | T | G | T | G | 0 | AA | 00 |
| 32 | A | T | T | G | T | G | 0 | AA | 00 |
| Effect of Polymorphism | silent | C = $Ala_{210}$<br>T = $Val_{210}$ | silent | C = $Ala_{235}$<br>G = $Gly_{235}$ | silent | G = $Ala_{342}$<br>C = $Thr_{342}$ | | | |

In Table 1, above, the nucleotide residues at 6 polymorphic positions are presented for all of the animals used in this study. Phenotype was determined serologically. Sequence type refers to which residues were found in the specificity-determining region, specifically positions 796, 803, and 813. Genotype was inferred from phenotype and sequence type as described in the text. The animals are grouped by putative prototype O allele and subgrouped by phenotype.

Genomic DNA isolated from peripheral blood lymphocytes was used as template for the polymerase chain reaction with three primer pairs, UPF-LPC, UPex5L-LPC, and UPH-Uaftx7b. The expected products, a 630 bp central segment of exon 7, an ~2.3 kb segment stretching from exon 5 through most of exon 7, and a 315 bp segment including the 3'end of exon 7, respectively, were obtained and used as templates in automated fluorescent sequencing. Even using a touch-down cycle, PCR of UPH-Uaftx7 generated many extraneous bands and required gel purification prior to sequencing. Representative sequences of exons 6 and 7 are presented in FIG. 1.

Figure 1C:
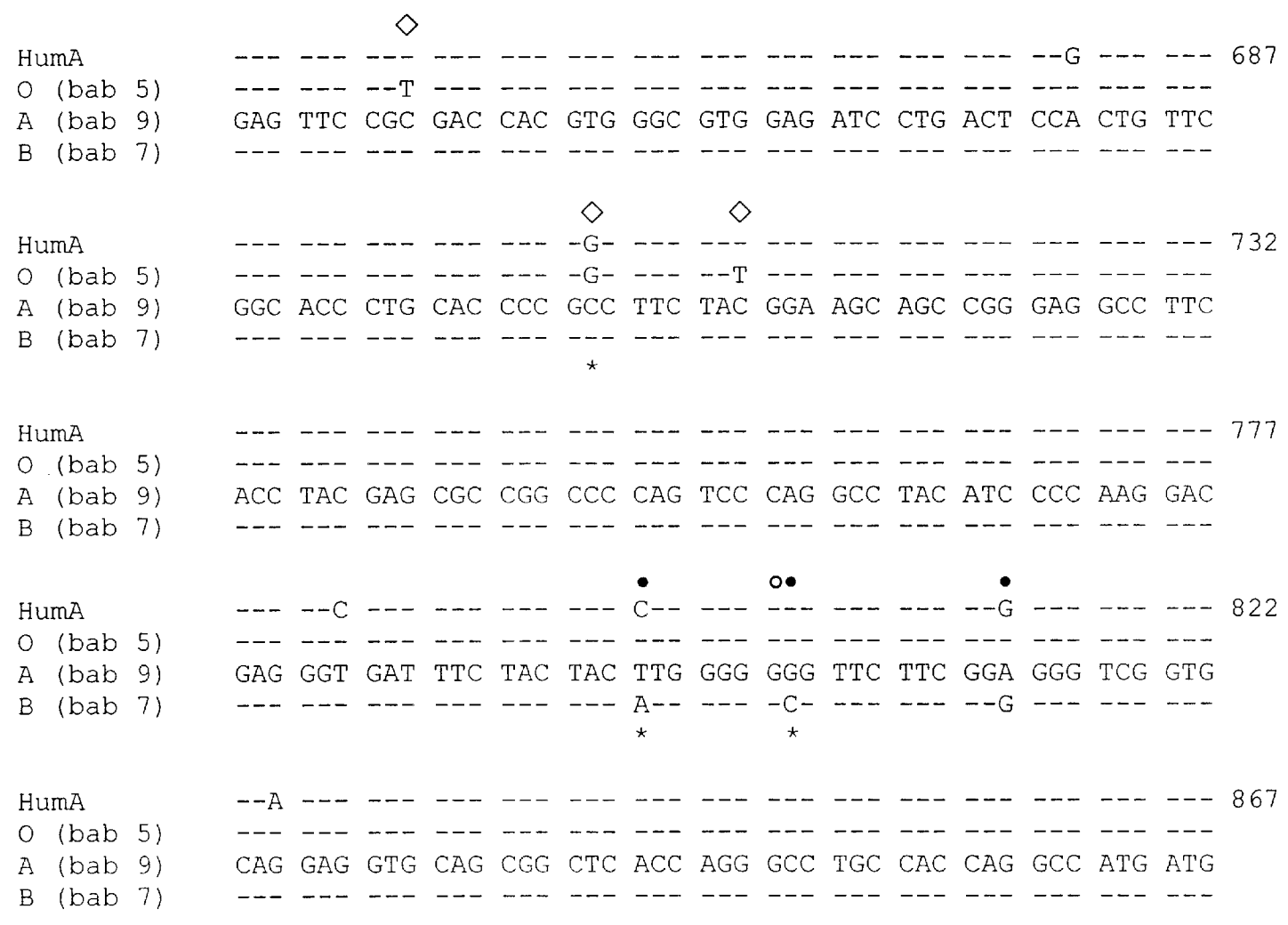

In FIG. 1, the sequences of exon 6 and exon 7, through the termination codon, of representative homozygous baboons of each blood group are aligned with each other and with the published sequence for human A transferase. The sequence from the group A baboon is explicitly presented, as are differences from it in the other three sequences; identical bases are indicated by a hyphen (-). The boundary between the two exons is indicated by a vertical line (|). Each position where a different amino acid is encoded by the different sequences is marked with a star (*) below the sequences. The three nucleotides used to classify baboon sequences as either A-like or B-like (i.e. sequence type) are marked with bullets (•), and the four nucleotide positions useful in distinguishing the baboon major O allele are marked with diamonds (◇), above the sequences. The positions of the deletion and substitution defining the human major and minor O alleles are marked with Δ and O, respectively.

As FIG. 1 shows, three nucleotide differences are consistently found between blood group A and B: $T_{796}$, G803, and $A_{813}$ in A become A,C, and G, respectively, in B. The first two differences result in the $Leu_{266}$>Met and $Gly_{268}$>Ala amino acid substitutions crucial for conversion between A and B transferase activity. The third difference is silent.

DNA sequence from the blood group O baboon (number 5) resembled that of baboon group A at the positions described above. Neither the $G_{261}$ deletion nor the $G_{802}$>A ($Gly_{268}$>Arg) mutation found in human O alleles was present. Four nucleotide differences from the baboon A/B consensus were observed. Two, $C_{651}$>T and $C_{711}$>T, are silent. The other two, $C_{629}$>T and $C_{704}$>G, cause $Ala_{210}$>Val and $Ala_{235}$>Gly amino acid changes, respectively. See Table 1. We also identified a second group O baboon (number 32) exhibiting these same sequence features.

The $Val_{210}$ and Gly235 residues seen in baboon blood group O are not immediately compelling candidates as the causative mutations of the phenotype; both of these residues are observed in a wide array of other primates. Martinko et al. (1993); Kominato et al. (1992). However, $Ala_{210}$ (the non-O residue) is unique to baboon; $Ala_{235}$ is uncommon among primates, but is not entirely unique to baboons—it is also seen in macaque. Kominato et al. (1992). It is interesting to note that the particular amino acid residue present at position 235 does have some effect on enzymatic activity in humans, where it is serine for human group B and glycine for human group A as it is for baboon group O. Yamamoto & Hakomori (1990); Yamamoto et al. (1990); Yamamoto, F., McNeill, P. D., Yamamoto, M., Hakomori,S., & Harris, T. (1993) Vox Sang 64:171–174. Nonetheless, the occurrence of $Gly_{235}$ in an unusual functional baboon allele (see below and Table 1) would seem to rule it out as the inactivating mutation. To the contrary, $Val_{210}$ has not been observed in a definitively active allele in baboon (see below and Table 1). Moreover the unique occurrence of Ala at this position in both active forms of the baboon enzyme may reflect selection for a residue which has become obligatory in that species.

Heterozygotes

We realized that, even without identifying the causative mutation for the baboon O phenotype, it would be possible to determine the genotype of serologic-group B phenotype individuals as either B/B or B/O based on the A-like sequence of the O allele. This screening would also allow us to evaluate the usefulness of the four nucleotide differences seen in the O homozygote as markers for the O allele. To accomplish this we concluded that all serologic-group B phenotypes that appear to be AB genotypes must be B/O heterozygotes. Since we simultaneously sequenced a mixture of both alleles from single individuals, we could not definitively resolve multiple heterozygosities. However, we interpreted these sequences as resulting from two alleles each of which most closely resembles one of the alleles found in the homozygotes above. For example, an animal with heterozygosities at $N_{796}$ and $N_{803}$ would be interpreted as having an A/B genotype, rather than being interpreted as having a pair of reciprocal A-B chimeric alleles.

By the above criterion, 7 of 22 blood group B phenotype baboons (4 of 14 males and 3 of 8 females) were determined to be B/O heterozygotes (Table 1). Examining these 11 O allele sequences (from the 7 B/O heterozygotes and the 2 O/O homozygotes), we observed that $nucleotide_{629}$ was a T (instead of C) in 9 of the 11 cases, as were $N_{651}$ and $N_{711}$. Similarly, $N_{704}$ was a G (instead of C) in 9 of these 11 cases. All of the B alleles had a C at $N_{629}$ and $N_{651}$. However, in baboon 18 $N_{704}$ and $N_{711}$ were homozygous, indicating that the B allele was similar to the O allele with a G and a T at these positions, respectively. Subsequently, DNA from these animals was sequenced using an A/O allele-specific primer, RASAO, positioned at the specificity-determining nucleotides. By using this primer to generate sequence data specifically from the A-like allele we were able to confirm that the O-like residues at $N_{480}$, $N_{629}$, $N_{651}$, $N_{704}$, and $N_{711}$ were indeed all in the A-like allele.

These observations bear on whether the amino acid substitutions caused by $C_{629}>T$ and $C_{704}>G$ are responsible for inactivating the O allele. The unusual B allele from the B/O heterozygote baboon 18 must be functional, indicating that $Gly_{235}$ (resulting from $C_{704}>G$ and homozygous in this animal) cannot be the inactivating mutation of the O allele, as alluded to above. Assuming that all of these O alleles derive from the same prototype O allele, the occurrence (in baboons 3 and 16) of two apparent O alleles that do not have either of these substitutions also implies that the causative mutation(s) lie elsewhere.

An alternate interpretation that we offer is that the alleles seen in baboons 3 and 16 represent a different prototype and underlying defect than found in the O homozygotes. Certainly it has been the case with rare human phenotypes (e.g. $A_3$ and $B_3$), that they are genetically heterogeneous with only some of the alleles having mutations identified by sequencing the same region we have sequenced here. Moreover, the weak activity encoded by $A_3$ alleles is apparently due in some cases to a $F_{216}>I$ substitution. This lends credence to the idea that relatively conservative amino acid substitutions in this region can significantly alter enzymatic activity and that $Ala_{210}>Val$ does account for the lack of enzymatic activity (in those alleles where it occurs). In any event, this possibility is not excluded by our data.

Even if the nucleotide differences observed in the O homozygotes do not explain their phenotype, they do exhibit enough linkage that it was possible to screen for putative A/O heterozygotes. By this criterion, 2 of 6 group A baboons (all female) were O heterozygotes (Table 1). All four positions where nucleotide differences were observed in the O homozygote were heterozygous in these animals. Unlike the group B animals above, the phenotype of these animals is not informative in deducing their genotype.

To our surprise, 1 of the 6 serologic group A animals (baboon 30) gave an apparent genotype of AB based on the sequence at nucleotide positions 796, 803, and 813. Thus the B-like allele in this animal must not produce an active enzyme, i.e. it is an O allele. We have not been able to identify any differences from a wild type B allele but, as it clearly must be independently derived from the A-like O allele(s), it constitutes a additional baboon O allele prototype. A B-derived O allele has not been previously observed. In fact, while group O is not uncommon in chimpanzee, which exhibits group A but not B, it has not been found in gorilla, which is monomorphic for group B. Socha & Ruffié (1983).

In addition to the type-associated differences discussed above, several other polymorphisms, that were either less rigorously associated with type or represented individual variation, have been observed. $N_{1024}$ is polymorphic A/G; encoding either $Thr_{ACT}$ or $Ala_{GCT}$. $N_{1024}$ might always be G in the major O allele. Allele-specific PCR supports this assignment for baboons 6 and 8, but it remains ambiguous for baboons 1 and 2. However, this substitution was not sufficient to cause the O phenotype as it exists in demonstrably functional alleles in baboons 9,14,18,21,23,26,31, and 33 (Table 1), nor was it associated with reduced levels of antigen expression. It might nonetheless be a necessary component of the major O allele.

$N_{480}$, a silent position that is predominantly G but sometimes A, was invariably A in the major O allele in those animals in which it could be determined (i.e., baboons 6,8,14,18, and 21; see Table 1). A silent G/T polymorphism was observed at $N_{1056}$ but no significant pattern was discerned. Finally there were four single instance variations observed: in baboon 1, $G_{1010}$ was heterozygous G/A resulting in a conservative switch from Arg to Lys; and in baboon 18, $A_{681}$, $G_{1026}$ and $G_{0062}$ are all heterozygous G/A, but the resulting codons are synonymous.

Comparison with Human Sequences

The baboon and human group A sequences from FIG. 1 are 96.5% identical, differing at 29 of the 826 positions (including the baboon polymorphism at $N_{1024}$ as a difference). Twenty-four of these substitutions are silent, including all 6 found in exon 6. The predicted amino acid sequences thus differ at 5 of 274 residues (all in exon 7), for 98.2% identity. Comparing group B sequences (using the human B allele sequence as reported in Yamamoto (1995)) reveals 31 nucleotide differences, 27 of which are the same as seen in the A to A comparison, and six amino acid differences, including the five positions where the group A sequences differ, though at one of these positions (amino acid 235) a different residue is involved as noted above. Thus comparing the group B sequences, there was 96.2% and 97.8% identity for nucleotides and amino acids, respectively.

Phylogeny

We have examined the phylogenetic relationship between the alleles at the ABO locus using our data on baboon along with previously published sequences for several other primate species. Yamamoto, (1995); Kominato et al. (1992). FIG. 2 presents the majority rule parsimony tree (which conveys branching order) for this locus. Based on the cladogram of FIG. 2, A-type activity would be predicted for the chimpanzee, orangutan, and macaque sequences, and B-type activity for the gorilla sequence. PIGGGTA, the related a-1,3-galactosyltransferase of *Sus scrofa*, was used as an outgroup. Previous distance analysis found evidence of transpecies evolution of the A and B alleles in the hominoids: human, chimp, gorilla, and orangutan. Martinko et al. (1993). Our analysis concurs that A and B arose prior to the split in the hominoid lineage and continued to evolve in parallel under similar selective forces. Our analysis does differ in the placement of orangutan, reflecting the different methodologies of parsimony versus distance.

It is clear that the divergence of the two old world monkeys, baboon and macaque, from the great apes preceded the origin of distinct A and B alleles in either group. Rather, the shared pair of enzymatic activities in these two major primate lineages is an example of convergent evolution. Accepting that B-like activity was ancestral (Socha & Ruffié (1983)), the use in A alleles of $CTG_{Leu}$ in the old world monkeys versus $TTG_{Leu}$ in the hominoid lineage at group-determining codon 266 is illustrative of analogy, not homology. Unlike the hominoid lineage, the establishment of distinct A and B alleles among baboon and macaque does not appear to have preceded the splitting off of the old world monkey species. The grouping of the major baboon O allele with macaque alleles implies that this branch most resembles the ancestral sequence since, as a non-functional gene, the sequence of O is not subject to selection and its similarity to macaque must therefore predate speciation. The baboon A and B transferases must have experienced a selective pressure causing them to diverge similarly from the ancestral sequence.

The absence of the mutations found in the human O alleles from the baboon O alleles, as well as the derivation of the baboon alleles from both an A and a B allele, demonstrates the independent origin of the O phenotype in these species. The appearance of the O phenotype, and in particular its prevalence in humans, combined with the loss of the B phenotype in chimpanzee and the A phenotype in gorilla (Socha & Ruffié (1983)), raises the prospect that this locus is no longer under strong selective pressure in the hominoid lineage. However since our data suggest that O alleles have arisen multiple times in baboon while the phenotype has remained rare, selection still may be operating at this locus in baboon. Nonetheless, group O baboons appear healthy, so it should be possible to breed a population of them to serve as universal histo-blood group organ donors in xenotransplantation efforts.

The genetic markers we have discovered will enable ABO genotyping for various purposes such as, for example, the identification of O heterozygous animals, screening of embryos, and quality control of semen for in vitro fertilization purposes.

One aspect of the present invention provides an isolated polynucleotide encoding an O allele of baboon. Polynucleotides of this aspect of the invention include all forms of O alleles in baboon such as those disclosed in this specification, and variants thereof that likewise are associated with the O phenotype. The polynucleotides may exist in a purified form or in a sequencing, cloning, or other vector. They may be used to analyze the genotype of a candidate for organ donation or for a breeding program, or they may be used in a recombinant construct for genetic manipulation of various mammalian cells and tissues.

This aspect of the invention contemplates that such cells and tissues would be used for organ transplantation, bone marrow transplantation, and blood, serum or platelet transfusion. Embodiments of this aspect of the invention include O alleles of baboon derived from either the A allele or the B allele.

An A-like allele is one that displays the characteristic A-like nucleotides at the positions that consistently distinguish the A and B alleles, and a B-like allele has the characteristic B-like nucleotides at the same positions. As shown in FIG. 1, these positions are $N_{796}$, $N_{803}$, and $N_{813}$. For example, an inactive allele having nucleotides $T_{796}$, G803, and $A_{813}$ would be classified as an A-like O allele. An inactive allele having nucleotides $A_{796}$, $C_{803}$, and G813 would likewise be considered to be a B-like O allele. One preferred embodiment of this aspect of the invention is the polynucleotide disclosed herein as SEQ ID NO:2. This sequence corresponds to an O allele mutation of the major A allele. Recombinant constructs of this aspect of the invention may preferably include all or part of any O allele, whether the allele is an A-like O allele or a B-like O allele, or whether the O allele differs from or is a combination of both the A and the B sequences at the characteristic positions discussed above.

These sequences may be combined with any of several kinds of DNA sequences in the recombinant constructs of the invention. Nonlimiting but representative examples of appropriate kinds of DNA sequences include plasmid cloning vectors, expression vectors, antisense vectors, minichromosomes, yeast artificial chromosomes, cosmid vectors, and phagemid vectors. A vector of the invention is any sequence that flanks the polynucleotides of the invention, and need not be a polyfunctional or self-replicating unit. Accordingly, a vector may be, for example, a promoter or promoter fragment suitable for attachment to a polynucleotide of the invention.

This aspect of the invention also encompasses other polynucleotides capable of hybridizing to critical regions of ABO alleles of baboon. Such polynucleotides have an important function in identifying individual carriers of the O allele and also in identifying such useful repositories of the O allele as embryos, tissues and other biological samples. Useful tissues in this aspect of the invention include, for example, both the cellular and extracellular fractions of blood and semen. Accordingly, oligonucleotides that are derived from the sequences disclosed herein, and that are used for such assay techniques, are considered to be part of the present invention.

Polynucleotides useful in this aspect of the invention include those capable of hybridization with baboon O alleles, with the polymorphic regions of the ABO locus, or with, for example, critical regions of SEQ ID NO:2. Non-limiting examples of such oligonucleotides are provided as SEQ ID NO:5, SEQ ID NO:15, SEQ ID NO:16, SEQ ID NO:17, SEQ ID NO:18, SEQ ID NO:19, SEQ ID NO:20, SEQ ID NO:21, and SEQ ID NO:22. It will be appreciated by one of ordinary skill in the art that additional oligonucleotides could be designed and screened for useful homology without undue experimentation and within the scope of this disclosure. Such oligonucleotides may also include PNA (peptide nucleic acid) nucleotides as discussed in Perry-O'Keefe, H., Yao, X.-W., Coull, J. M., Fuchs, M., & Egholm, M. (1996) *Proc. Nat. Acad. Sci. USA*, 93:14670–14675. PNA is a DNA mimic with a neutral peptide-like backbone, and the hybridization of PNA oligomers to complementary DNA is essentially independent of the ionic strength of the hybridization buffer, due to the neutral backbone of PNA. Thus, a PNA oligomer will hybridize to a complementary DNA oligomer under conditions where DNA/DNA hybridization is strongly disfavored, such as at low ionic strength. Also, because the PNA backbone is neutral, the electrophoretic mobility of PNAs primarily is a function of size, and unhybridized PNAs accordingly migrate much more slowly than DNA in an electric field. The migration of PNA under assay conditions largely depends on the extent of hybridization between the PNA and the target DNA. The present invention contemplates the use of PNA oligomers as probes, and any reference herein to oligonucleotide or polynucleotide probes may preferably include probes that are either complete or partial oligomers of PNA.

In another aspect of this invention, a method is provided for detecting an allele of histo-blood group O in a biological sample. One embodiment of this method includes the steps of isolating nucleic acids from a biological sample and screening the sample for presence of the allele by any of several techniques, making use of at least a region of, for example, SEQ ID NO:5, SEQ ID NO:15, SEQ ID NO:16, SEQ ID NO:17, SEQ ID NO:18, SEQ ID NO:19, SEQ ID NO:20, SEQ ID NO:21, or SEQ ID NO:22 which are an allele-specific probes or allele-excluding probes. For example, a blood sample may be analyzed by extracting DNA therefrom and screening the DNA in a hybridization assay for close homology to at least 12 contiguous nucleotides of an allele-specific probe. Hybridization may be measured by any of several indicators, including gel shift, nuclease protection, Southern, northern, slot, or dot blotting, polymerase chain reaction (PCR), ligase chain reaction (LCR), or self-sustained sequence replication (3SR). Other biological samples contemplated for use in this aspect of the invention include cells and cell cultures, embryos, fetuses, gametic or gonadal cells, whole organs, and tissues. Tissues include, among numerous others, blood and semen.

Also contemplated in this aspect of the invention is the use of the isolated polynucleotides in techniques for screening nucleic acids without rigorous purification procedures, including in situ or other in vivo assays. The method of this aspect of the invention may also be applied to fluorescence activated cell sorting wherein cells, such as gametic cells or zygotes, that harbor an O allele, may be identified and separated from cells that do not harbor an O allele.

In a related aspect of the present invention, a method is provided for screening a mammal to determine whether the mammal carries an allele of histo-blood group O. The method begins with a candidate individual known to be phenotypically histo-blood group A or histo-blood group B. There are several ways of determining histo-blood group, such as forward and reverse typing as discussed in this disclosure. Determination of phenotype may also be inferred from knowledge of an individual's pedigree, from linkage analysis, allele frequency probabilities, and the like.

The objective of this first step in the present method is to eliminate from subsequent steps those individuals of blood group AB. This is because an individual of blood group AB is certain not to be a carrier of any O alleles except in very rare cases of aneuploidy or cis-A/B mutations. As will be appreciated from the discussion of Hardy-Weinberg models in the background of the present disclosure, the more rare the O allele as a proportion of the allele pool for the ABO locus, with the attending greater preponderance of the A and B alleles, the more proportional benefit will be derived from preselecting and eliminating AB individuals from subsequent steps of the method of the invention. This is because, as A and B alleles individually occupy a larger proportion of the entire allele pool, AB heterozygotes are a proportionally larger repository of undesired A and B alleles.

Having eliminated AB individuals by selecting only group A or group B candidates, the next step of screening nucleic acids of group A and group B individuals may be performed. The purpose of the screening step is to determine whether the group A or group B individuals are homozygous or heterozygous. Like the AB individuals discussed above, A/A homozygotes or B/B homozygotes carry no O alleles. It is therefore desirable to eliminate from subsequent steps in the present method any homozygous A or homozygous B individuals as may be detected in the screening step of the method of this aspect of the invention.

Nucleic acids of candidate individuals may be screened by using the polynucleotides of the present invention in any of several ways as discussed herein. It is important to note that one need not detect with high fidelity the presence of an O allele in this step. It is sufficient to find an allele sequence that is discordant with the phenotype. For example, an A-like allele is discordant with a B phenotype, and a B-like allele is discordant with an A phenotype. This is because an apparent B allele in an A individual clearly does not contribute to that individual's phenotype, and therefore must be an inactive derivative of the B allele.

It is known from the results disclosed herein that there exist O alleles of baboon derived both from B alleles as well as from A alleles. Accordingly, it is sufficient in the screening step of this aspect of the invention to detect any apparently non-functioning allele based on a discordance comparison of the genotype information from the screening step with the known phenotype of the individual.

An additional step of this embodiment of the method of the invention is to compare the apparent genotype with the predetermined phenotype and to identify thereby carriers of O alleles (i.e., inactive A-like or inactive B-like alleles). The invention contemplates that the screening step may involve the use of the isolated polynucleotides of the invention such as, for example, those disclosed as SEQ ID NO:5, SEQ ID NO:15, SEQ ID NO:16, SEQ ID NO:17, SEQ ID NO:18, SEQ ID NO:19, SEQ ID NO:20, SEQ ID NO:21, and SEQ ID NO:22.

Another aspect of the invention is a kit for detecting an allele of histo-blood group O. The kit of the invention has several useful embodiments. It includes a nucleotide useful for detecting the desired allele as disclosed herein, as well as other indicia of the presence of the O allele. Such indicia may be color reagents, thermal indicators, electrical conductors, biochemical intermediates, or fluorescent reagents. A preferred embodiment of the kit of the invention is a field-ready assay device adapted for quick analysis of buccal scrapings or other cells of a primate specimen, or a laboratory-oriented, reusable or disposable device for simplified analysis of the genotype of an individual mammal.

In another aspect of the invention, a method is provided for producing a histo-blood group O non-human primate. This method begins with a male and female non-human primate, each of which is known to carry a group O allele. The O carrier individuals to be mated may be determined to be O carriers by one of several methods, including pedigree analysis, phenotype/genotype analysis as discussed above, and detection of an O allele. Gametes of the male and female group O allele carriers are combined. Subsequent progeny of the combination of gametes are selected for homozygosity of the O allele. The progeny of the cross of this method of the invention may be selected in embryonic stages, and in some cases multiple progeny may be propagated from one embryo.

In one embodiment of this step of the method of the invention, an embryo is scraped to remove one or a few cells, and DNA is extracted from the cells thus removed. The embryos preferably may be at a developmental stage of from 8 to 32 cells. PCR analysis or some other amplification and screening technique is applied to the DNA thus extracted. Those individuals shown by this assay to be homozygous O/O will be cultured to subsequent embryonic stages and implanted for gestation in a surrogate non-human mammal. Embryos shown to be heterozygous A/O or B/O or homozygous A or B will be removed from subsequent steps.

This method provides a way of increasing the efficiency and yield of group O individuals from matings of non-O parents. As discussed above, typical matings of non-AB, non-O individuals will produce small and only incrementally manipulable numbers of O offspring. However, with the present method as disclosed herein, the only inefficiency in the yield of group O individuals would be a function of the homozygosity detection method. While screening of embryos and implantation into surrogates is an expensive and involved process, the benefit of obtaining close to 100 group O individuals per 100 matings, instead of only about 2 individuals of group O per 100 matings, is evident.

This aspect of the invention is further embodied in a method to produce a histo-blood group O strain of non-human primate beginning with an individual non-human primate as produced in the method of this aspect of the invention, and crossing the group O individual with another group O individual to produce the desired group O strain. Since both parents in such a mating are group O homozygotes, all offspring of such a mating will likewise be group O, barring vanishingly rare events of reverse mutation. Accordingly, no gametic, zygotic, or embryonic screening step is required. The production and propagation of a group O strain may be facilitated by in vitro fertilization and embryo culturing techniques.

The group O strain produced in this aspect of the invention also contemplates individual non-human primates of the strain, as well as organs and tissues derived therefrom, particularly for xenotransplantation from individuals of the strain to human patients with severe medical needs. In addition to xenotransplantation uses, individuals of the strain of this aspect of the invention are important for breeding to increase the numbers in a group O colony or population.

In another aspect of the invention a method is provided for genetically modifying a non-human primate to produce an individual of histo-blood group O. This method begins with a target cell sample from a non-human primate. Such a target cell sample could be a gonadal cell, a gamete, an embryo, or an intact individual. The step involves transfecting the biological sample with a recombinant construct that includes a polynucleotide of the present invention. An additional step involves modification of the genotype of the biological sample by the action of the recombinant construct.

Transfection of biological samples may be mediated by electroporation, PEG-mediated transfection, viral vector transfection, lipid-mediated transfection, and like techniques. The action of the recombinant construct that results in a modification of the genotype of the sample may be antisense binding of messenger RNA for non-O alleles of the ABO locus. The action of the recombinant construct may also result in homologous recombination between a segment of the construct and a chromosomal region housing all or part of the ABO locus. A preferred recombinant construct for homologous recombination may be an RNA/DNA chimera. Additionally, the recombinant construct may contain a ribozyme such as, for example, modified ribozymes having sequence regions complementary to a desired sequence region of ABO alleles. Other actions of recombinant constructs that would result in a modification of the genotype would be, for example, transposon mutagenesis or other interruption of a promoter region or an exon of the non-O allele sequence.

Also contemplated as embodiments of this aspect of the invention are individuals modified by this method to be phenotypically group O, as well as a strain of genetically modified non-human primates of histo-blood group O produced by the method of this aspect of the invention. Likewise contemplated as part of the invention is an organ or tissue or other biological sample from an individual of such a strain of group O individuals produced by genetic manipulation using a construct of the present invention.

EXAMPLE 1

Serologic Phenotyping

Using ketamine anesthesia (15 mg/kg), 10 ml heparinized (100 U/ml) and 5 ml clotted blood were collected from the femoral vein of the baboons tested. Buccal mucosa epithelial cells were also collected by swabbing the buccal mucosa and applying the cells to a glass slide. The slides were then dried overnight. Direct typing was performed using the standard immunophenotyping assay with immunofluorescent-stained scrapings of the buccal epithelium. Nehlsen-Cannarella, S. L. & Bohn, M. (1987). Conventional reverse typing may also be performed using baboon serum (pre-adsorbed with human blood group O erythrocytes) to agglutinate human A and B type erythrocytes.

EXAMPLE 2

DNA Isolation, Sequencing and Analysis

DNA Isolation

Peripheral blood lymphocytes were isolated from whole blood by ficoll gradient centrifugation and used as a source of genomic DNA. DNA isolation was carried out using either the RapidPrep™ Macro Genomic DNA Isolation Kit (Pharmacia), initially, or the QIAamp Blood Kit (Qiagen) according to the manufacturers' directions.

Polymerase Chain Reaction

PCR primers were designed based on the human ABO sequences. Three upstream and two downstream primers were used for amplification of genomic DNA: UPex5L, GATGGTCTACCCCCAGCCAAAGGTGCT (SEQ ID NO:6), covering most of exon 5; UPF, TGGGCCACCGTGTCCACTACTATGTCTT (SEQ ID NO:7), located toward the 5' end of exon 7; UPH, CCAAGGACGAGGGTGATTTCT (SEQ ID NO:8), located centrally in exon 7; LPC, TCCGGACCGCCTGGTGGTTCTTG (SEQ ID NO:9), located near and complementary to the 3' end of exon 7; and Uaftx7, AGCCCTCCCAGAGCCCCTGG (SEQ ID NO:10), located in the untranslated region shortly after the stop codon. UPF-LPC reactions contained each primer at a concentration of 0.5 μM, 300–500 ng genomic DNA, dNTPs at a concentration of 200 μM each, pfu polymerase (2.5 units) (Stratagene), and the supplied buffer, in 100 μl. Typical thermocycling conditions were: denaturation at 94° C. for 2 min.; 30 cycles at 94° C., 5 sec., 55.9° C., 30 sec., and 72° C. for 2.5 min.; followed by 72° C. for 7 min. on a GeneAmp PCR System 9600 (Perkin Elmer). A hot start was achieved by adding enzyme while paused at the first annealing step. UPex5L-LPC and UPH-Uaftx7 reactions contained each primer at a concentration of 0.41 μM, respectively, 200 ng genomic DNA, dNTPs at a concentration of 350 μM each, Expand Polymerase—a mixture of Pwo and taq polymerases— (2.6 units)(Boehringer-Mannheim) and supplied buffer 1, in 50 μl. For UPex5L-LPC typical thermocycling conditions were: denaturation at 94° C. for 2 min.; 30 cycles at 94° C., 5 sec., 56° C., 30 sec., and 68° C. for 4 min. plus 20 sec. each cycle for the 20; followed by 68° C. for 7 min., on a GeneAmp PCR System 9600 (Perkin Elmer). UPH-Uaftx7 required a touchdown cycle: denaturation at 94° C. for 2 min.; 20 cycles of 94° C., 5 sec., 66° C., 30 sec., reduced one degree each cycle; 68° C., 5 min.; 20 of 94° C., 5 sec., 46° C., 30 sec.; 68° C., 4 min. plus 10 sec. each cycle; followed by 68 °C. for 7 min., on a PE9600. Hot starts were achieved in the same manner. Success of reactions was judged by agarose gel electrophoresis.

DNA Sequencing

PCR products were purified either directly from the reaction (UPF-LPC and UPex5L-LPC) or from agarose gel slices (UPH-Uaftx7) using QIAquick spin columns (Qiagen) and then used directly in cycle sequencing using an Applied Biosystems 373A and Amplitaq CS (initially) or FS. Additional primers used for sequencing were: LPex6al, TTGATGGCAAACACAGTTAACCCAATGG (SEQ ID NO:11), located near and complementary to the 3' end of exon 6; IB4x6, AGAGGAGGCGGAAACTGAG (SEQ ID NO:12), located in the intron upstream of exon 6; IB4x7b, TCTGAGCCTTCCAATGTCCGCTG (SEQ ID NO:13), located in the intron upstream of exon 7; and LPm7, GTCCACGCACACCAGGTAATCCAC (SEQ ID NO:14), located centrally in and complementary to exon 7. Unlike the other primers, IB4x6 and IB4x7b were both designed from baboon intronic sequences. DNA from representative animals was sequenced with the complete primer set. Additional animals screened for heterozygosity were generally sequenced with only the primers UPH and UPF initially. DNA from all of the screened animals thus identified as heterozygotes was further amplified and sequenced with UPH and Uaftx7b. Finally, an allele-specific primer, RASAO, ACCGACCCCTCGAAGAACCCCCCAA (SEQ ID NO:5), located so that its 3' end paired with $N_{796}$ of A-like alleles, was used to resolve multiple heterozygosities as appropriate.

Phylogenetic Analysis

Representative nucleotide sequences, spanning positions 435–1003, were aligned using the ClustalW server at Baylor College of Medicine. Thompson, J. D., Higgins, D. G. & Gibson, T. J. (1994) Nucleic Acids Res. 22:4673–4680. The aligned sequences were then subjected to parsimony analysis using PAUP version 3.1. Swofford, D. (1993) *Phylogenetic Analysis Using Parsimony User's Manual* Illinois Natural History Survey, Champaign, Illinois. A consensus tree was constructed using the 50% majority rule option. An aligned segment of *Sus scrofa* α-1,3-galactosyltransferase was explicitly used as an outgroup. See Strahan, K. M., Gu, F., Preece, A. F., Gustavsson, I., Andersson, L. & Gustafsson, K. (1995) *Immunogenetics* 41:101–105.

EXAMPLE 3

Assays for Presence of the O Allele

The sequence of the O allele, as well as the A and B alleles, may be used in several assays to detect the presence of the O allele in biological samples.

Hybridization

An oligonucleotide capable of spanning a region of difference between the O and A/B alleles is synthesized. Based on the sequence of the oligonucleotide, appropriate buffer and temperature conditions are selected such that only the perfect match hybridizes. Preliminary determination of a suitable temperature and buffer may employ the formula: $T_m$=81.5° C.+16.6($\log_{10}$[$Na^+$])+0.41(fraction G+C)−0.63(%formamide)-(600/1) where 1 is the length of the hybrid in base pairs. This formula and other guidelines for selecting hybridization conditions are provided in Sambrook, J., Fritsch, E. F., and Maniatis, T., *Molecular Cloning* (Second Edition) Cold Spring Harbor Laboratory Press, 1989.

A more sophisticated approach to optimization of hybridization conditions is available with use of "nearest neighbor" sequence analysis. There are several nearest neighbor software applications known in the art, a preferred one being "Oligo," available from National Biosciences, Incorporated, of Plymouth, Minn. The oligonucleotide is used under these selected conditions in hybridization protocols such as Southern, northern, slot or dot blots, as well as solution phase hybridizations. Detection is accomplished via labeled probe or, where the target is generated by PCR, detection is accomplished with the use of labeled PCR product. The presence of the O allele is determined by hybridization assays using the O-specific probe alone. Presence of the O allele is also detected by employing parallel hybridization protocols using both O- and A/B-specific probes to distinguish heterozygotes from homozygotes. Presence of the O allele may also be detected with an endonuclease that specifically recognizes a sequence unique to an O allele. Alternatively a restriction enzyme that specifically recognizes and cleaves a sequence found in non-O allele, but not in O alleles, may also be used to distinguish between O and non-O alleles.

In some procedures both O-specific and A/B-specific probes are used together. Examples include a protection assay using differently labeled fluorescent probes and a capture assay using probes labeled with different ligands.

PNA Probes

Allele-specific PNA probes are constructed and are labeled with fluorescent markers such that the A-specific probe is red, the B-specific probe is blue, and the probe specific to the major (A-like) O allele is yellow. These labeled probes are used to determine the genotype of a biological sample. Assignment of fluorescence color for probes is arbitrary and is provided herein for convenience. A variety of fluorescence labels is known to those of ordinary skill in the art.

Nucleic acids from a biological sample are amplified by PCR, and then subjected to hybridization conditions and are exposed to all three labeled PNA probes. After hybridization, the nucleic acids are assayed for the color and intensity of any bound probes. A control is measured to standardize relative intensity levels of each color. A sample with equal relative intensity signals of blue and red, but no yellow, is interpreted as having a genotype of A/B. A sample from an A/O individual, wherein the O allele is the major, A-like, O allele, displays red and yellow labels, with the red being twice as intense as the yellow. With the probes as described above, a sample from an individual known to have a group O phenotype displays all three colors in equal relative intensity. The interpretation is that the individual has one A-like O allele to which the red and yellow bind in equal ratios, and one B-like O allele which is bound by the blue-labeled probe.

In another use of PNA probes, a PNA probe is synthesized with a sequence corresponding to an A-like O allele, with the sequence spanning a region of difference between the O allele and the A allele. The probe strongly hybridizes to either allele in a buffer of low ionic strength. However, with the A allele, a single-base mismatch exists between the PNA probe and the DNA of the A allele. A mismatch-recognizing single strand endonuclease cleaves the DNA of the allele at the mismatch, and electrophoretic separation of the DNA fragments provides evidence of the mismatch cleavage. The cleavage indicates the presence of an A allele. In an A/O heterozygous individual, where the O allele is an A-like O allele, a dual electrophoretic pattern emerges, indicating that the individual is heterozygous, and that one allele sequence is cleaved in the presence of the probe and one is not.

Restriction Enzymes

The O, A, and B allele sequences are analyzed, and restriction sites are selected that are capable of generating restriction fragment length polymorphisms among the several ABO alleles. Genomic DNA from a biological sample is extracted and purified, then it is cleaved by the selected restriction enzyme. The cleavage products are resolved using agarose gel electrophoresis, and DNA isolates containing the O allele are identified based on the presence of the predicted polymorphic restriction fragments, as visualized in a Southern hybridization procedure using labelled probe.

In an alternative restriction fragment length polymorphism procedure, target DNA is amplified using standard PCR protocols. The amplified DNA is then cleaved with a selected restriction enzyme, and amplified ABO allele samples are analyzed for the presence of characteristic O-associated fragments in agarose gel electrophoresis.

In another use of restriction enzymes as diagnostic indicators of the O allele, ABO alleles in a biological sample are amplified by PCR, and the amplified product is treated with MaeIII, which selectively cuts DNA of the major O allele and not DNA of the A or B alleles. Presence of the O allele is manifest by the production of two fragments by the action of the allele-specific restriction reaction. As an example, a non-limiting list of several known restriction enzymes having specificities effective for distinguishing among baboon ABO alleles is provided in Table 2.

TABLE 2

| Position | Enzyme(s) | Basis for distinction among alleles |
|---|---|---|
| N629 | AciI, BstUI, HHaI | fail to cut the major O allele |
| N651 | AciI, BstUI | fail to cut the major O allele |
| N651 | MaeIII, Tsp45I | cut only the major O allele |
| N704 | AciI | fails to cut the major O allele |
| N704 | BsaJI, CviJI, HpaII, NciI, ScrFI | cut only the major O allele (and the rare B allele of Baboon 18) |
| N796 | NlaIII | cuts only B-like alleles |
| N813 | MnlI | cuts only A-like alleles |

Allele-specific PCR

Allele-specific PCR primers are designed to differentiate between O and non-O histo-blood group allele sequences under PCR conditions. These primers then amplify only a specific subset of possible ABO allele(s) in a biological sample. In one protocol, different allele specific primers are used singly in each of a series of PCR reactions, and the products of the reactions are analyzed to assess whether a given primer was effective in mediating the amplification of the target DNA.

In an alternative protocol, primers specific for different ABO alleles are multiplexed in a single PCR reaction. The primers are distinguished from one another by differences of length and/or by fluorescent labeling so that the different alleles that are thus amplified also have different sizes or colors.

Ligase Chain Reaction

Oligonucleotides suitable for LCR are synthesized and incubated with amplified ABO allele DNA containing one or more ABO allele sequences. The paired LCR probe ends are designed to match with one of the alleles and to have at least a one-base mismatch with the other allele(s). Ligation occurs only where there is a perfect match between both probe ends and the target sequence. A thermostable ligase is added to the reaction, and ligation products are quantified and measured. High accumulation of O-allele-specific ligation products indicates the presence of O allele in the biological sample from which the DNA was originally amplified. Complete typing is accomplished either through a set of individual reactions or via one multiplexed reaction wherein accumulated ligation products of different LCR probes are individually resolved and measured.

Self-sustained Sequence Replication

A single-stranded DNA oligonucleotide primer for 3SR ("first primer") is synthesized having a T7 promoter sequence at its 5' end. The 3' end of the primer has a sequence that is sequence complementary to the 3' end of mRNA from an allele of the ABO locus. Also synthesized is another single stranded DNA oligonucleotide primer ("second primer"). The second primer has a sequence that is identical to the 5' end of mRNA from an allele of the ABO locus.

RNA from a blood or tissue sample of baboon of group A or B (not AB) is added to a 3SR amplification mix containing the first and second primers, 6 mM of each rNTP, 1 mM of each dNTP, 30 units of avian myeloblastosis virus reverse transcriptase, 4 units $E.\ coli$ RNase H, and 100 units T7 RNA polymerase in a total volume of 100 $\mu$l. The mix of nucleotides and RNA is denatured for 1 minute at 65° C. prior to addition of the enzymes. After the enzymes are added, the reaction mix is incubated at 42° C. for 1 hour. The ABO allele mRNA is amplified to yield an analytically useful amount of double stranded cDNA, which is treated with an allele-specific restriction enzyme to determine the presence of absence of an O-allele, or to detect the presence of an apparent B allele in an individual of group A, or the presence of an apparent A allele in an individual of group B.

Gel Mobility

A polymorphic region of the ABO locus is amplified by PCR. The resulting PCR product is then denatured and cross-hybridized with the relevant portion of a defined allele. The hybridized DNA is then subjected to temperature gradient gel electrophoresis. Matched and mismatched hybrids display different mobilities under these conditions, and the mobilities of different samples are compared with control samples to identify the genotype of the amplified DNA. Alternatively the DNA hybrids are treated with a single-strand nuclease prior to electrophoresis. The DNA hybrids are thus cleaved at the site of any mismatch, and multiple fragments are generated. The presence, absence, and/or number of multiple fragments indicate the degree of mismatch between the sample DNA and the probes that correlate with known genotype.

In an additional protocol, the DNA is denatured before electrophoresis, and is loaded into the gel in its denatured state. Sequence variations within the single stranded DNA result in differential mobility under defined conditions. The mobility of unknown samples thus prepared is compared with that of samples of known genotype.

EXAMPLE 4

Oligonucleotides for Genotyping

Several oligonucleotides are designed to be useful for genotyping by methods such as, for example, one or more of the methods mentioned in this specification. Nonlimiting examples of some useful oligonucleotides are provided in Table 3. The oligonucleotides of this Example are DNA, RNA, or PNA, or chimeras of any two or all three of DNA, RNA, and PNA. While some of the oligonucleotides of Table 3 are longer than 12 nucleotides, a 12 nucleotide fragment of the longer nucleotides provided may be selected to carry out the desired genotyping procedure. PNA nucleotides are effective in shorter fragments than 12 nucleotides, depending on the presence of internal or terminal mismatches, and also depending on the hybridization conditions.

TABLE 3

| Sequence | Specificity | SEQ ID NO: |
|---|---|---|
| 5'-ACC903CCCCCAA796GTAGTA-3' | A-like alleles | 15 |
| 5'-ACG803CCCCCAT796GTAG-3' | B-like alleles | 16 |
| 5'-GGACGAGGGTGATTTCTACTACT796-3' | A-like alleles | 17 |
| 5'-CAAGGACGAGGGTGATTTCTACTACA796-3' | B-like alleles | 18 |
| 5'-ACCGACCCCT813CCGAAGAACC803CCCCCAA796-3' | A-like alleles | 5 |
| 5'-CGACCCCC813CCGAAGAACG803CCCCCAT796-3' | B-like alleles | 19 |
| 5'-TCCACGTCCA629CGCA | major O allele | 20 |
| 5'-CGC629GGACGTGGACATGGAGTTCCGC651- 3' | non-O alleles | 21 |
| 5'-GTGTGCGT629GGACGTGGACATGGAGTTCCGT651-3' | major O allele | 22 |

If discrimination among the ABO alleles is based on hybridization, any oligonucleotide spanning one or more of the critical positions is potentially useful. In preferred embodiments the mismatches are centrally located in the oligonucleotide sequence. If discrimination is based on primer extension or ligation, the mismatch is preferably positioned at the end of the oligonucleotide. For primer extension, the mismatch should be located at the 3' end of the oligonucleotide. Some effective oligonucleotides derive their sequence from the non-coding strand; where such oligonucleotides are used for primer extension, the mismatch is still preferably located at the 3' end. Discrimination of O from non-O (for the major O allele) can be based on positions 629, 651, 704, and 711. However, a method based on 704 and/or 711 alone would be expected to have a small but significant false positive rate due to the B allele of baboon 18.

EXAMPLE 5

Selection of Embryos

The genotype of adult baboons in a breeding pool is determined by one of the techniques described herein. Gametes are collected from the A/O and/or B/O heterozygotes thus identified, and embryos are produced by in vitro fertilization. One or a few cells are taken from embryos at the 8-, 16-, or 32-cell stage. Nucleic acids from the embryonic cells are screened to identify O/O homozygotes. Homozygous O/O embryos are preserved for implantation and gestation in suitable mature females. Progeny from this one-generation approach are all O/O homozygotes, and are used as xenotransplant donors, or for successive rounds of breeding with other group O individuals or with A/O or B/O heterozygotes to establish a group O colony of baboons.

What is claimed is:

1. An isolated polynucleotide, comprising the sequence as set forth in SEQ ID NO: 2.

2. A recombinant vector comprising the isolated polynucleotide of claim 1.

* * * * *

SEQUENCE LISTING (1) GENERAL INFORMATION:

(iii) NUMBER OF SEQUENCES: 22

(2) INFORMATION FOR SEQ ID NO: 1:

(i) SEQUENCE CHARACTERISTICS:
      (A) LENGTH: 826 base pairs
      (B) TYPE: nucleic acid
      (C) STRANDEDNESS: single
      (D) TOPOLOGY: linear (xi) SEQUENCE DESCRIPTION: SEQ ID NO: 1:

```
TAGGAAGGAT GTCCTCGTGG TGACCCCTTG GCTGGCTCCC ATTGTCTGGG AGGGCACATT    60

CAACATCGAC ATCCTCAACG AGCAGTTCAG GCTCCAGAAC ACCACCATTG GGTTAACTGT   120

GTTTGCCATC AAAAAATACG TGGCTTTCCT GAAGCTGTTC CTGGAGACGG CGGAGAAGCA   180

CTTCATGGTG GGCCACCGTG TCCACTACTA TGTCTTCACC GACCAGCTGG CCGCGGTGCC   240

CCGCGTGACG CTGGGGACCG GTCGGCAGCT GTCAGTGCTG GAGGTGCGCG CCTACAAGCG   300

CTGGCAGGAC GTGTCCATGC GCCGCATGGA GATGATCAGT GACTTCTGCG AGCGGCGCTT   360

CCTCAGCGAG GTGGATTACC TGGTGTGCGT GGACGTGGAC ATGGAGTTCC GCGACCACGT   420
```

```
GGGCGTGGAG ATCCTGACTC CGCTGTTCGG CACCCTGCAC CCCGGCTTCT ACGGAAGCAG    480

CCGGGAGGCC TTCACCTACG AGCGCCGGCC CCAGTCCCAG GCCTACATCC CCAAGGACGA    540

GGGCGATTTC TACTACCTGG GGGGGTTCTT CGGGGGGTCG GTGCAAGAGG TGCAGCGGCT    600

CACCAGGGCC TGCCACCAGG CCATGATGGT CGACCAGGCC AACGGCATCG AGGCCGTGTG    660

GCACGACGAG AGCCACCTGA ACAAGTACCT GCTGCGCCAC AAACCCACCA AGGTGCTCTC    720

CCCCGAGTAC TTGTGGGACC AGCAGCTGCT GGGCTGGCCC GCCGTCCTGA GGAAGCTGAG    780

GTTCACTGCG GTGCCCAAGA ACCACCAGGC GGTCCGGAAC CCGTGA                   826

(2) INFORMATION FOR SEQ ID NO: 2:

(i) SEQUENCE CHARACTERISTICS:
        (A) LENGTH: 826 base pairs
        (B) TYPE: nucleic acid
        (C) STRANDEDNESS: single
        (D) TOPOLOGY: linear (xi) SEQUENCE DESCRIPTION: SEQ ID NO: 2:

TAGGAAGGAC GTCCTTGTCG TGACCCCTTG GCTGGCTCCC ATTGTCTGGG AGGGCACGTT     60

CAACATCGAC ATCCTCAACG AGCAGTTCAG GCTCCAGAAC ACCACCATCG GGTTAACTGT    120

GTTTGCCATC AAAAAATACG TGGCCTTCCT GAAGCTGTTC CTGGAGACGG CGGAGAAGCA    180

CTTCATGGTG GGCCACCGCG TCCACTACTA CGTCTTCACC GACCAGCCGG CTGCGGTGCC    240

ACGCGTGGCG CTGGGGACCG GTCGGCAGCT GTCGGTGCTT GGGGTGCGCG CCTATAAGCG    300

CTGGCAGGAC GTGTCCATGC GCCGCATGGA GATGATCAGC GACTTCTGCG AGCGGCGCTT    360

CCTCAGCGAG GTGGATTACC TGGTGTGCGT GGACGTGGAC ATGGAGTTCC GTGACCACGT    420

GGGCGTGGAG ATCCTGACTC CACTGTTCGG CACCCTGCAC CCCGGCTTCT ATGGAAGCAG    480

CCGGGAGGCC TTCACCTACG AGCGCCGGCC CCAGTCCCAG GCCTACATCC CCAAGGACGA    540

GGGTGATTTC TACTACTTGG GGGGGTTCTT CGGAGGGTCG GTGCAGGAGG TGCAGCGGCT    600

CACCAGGGCC TGCCACCAGG CCATGATGGT CGACCAGGCC AACGGCATCG AGGCCGTGTG    660

GCACGACGAG AGCCACCTGA ACAAGTACCT GCTGCGCCAC AAACCCACCA AGGTGCTCTC    720

CCCCGAGTAC CTGTGGGACC AGCAGCTGCT GGGCTGGCCT GCGGTCCTGA GGAAGCTGAG    780

GTTCGCGGCG GTGCCCAAGA ACCACCAGGC GGTCCGGAAC CCGTGA                   826

(2) INFORMATION FOR SEQ ID NO: 3:

(i) SEQUENCE CHARACTERISTICS:
        (A) LENGTH: 826 base pairs
        (B) TYPE: nucleic acid
        (C) STRANDEDNESS: single
        (D) TOPOLOGY: linear (xi) SEQUENCE DESCRIPTION: SEQ ID NO: 3:

TAGGAAGGAC GTCCTTGTCG TGACCCCTTG GCTGGCTCCC ATTGTCTGGG AGGGCACGTT     60

CAACATCGAC ATCCTCAACG AGCAGTTCAG GCTCCAGAAC ACCACCATCG GGTTAACTGT    120

GTTTGCCATC AAAAAATACG TGGCCTTCCT GAAGCTGTTC CTGGAGACGG CGGAGAAGCA    180

CTTCATGGTG GGCCACCGCG TCCACTACTA CGTCTTCACC GACCAGCCGG CTGCGGTGCC    240

GCGCGTGGCG CTGGGGACCG GTCGGCAGCT GTCGGTGCTT GGGGTGCGCG CCTATAAGCG    300

CTGGCAGGAC GTGTCCATGC GCCGCATGGA GATGATCAGC GACTTCTGCG AGCGGCGCTT    360

CCTCAGCGAG GTGGATTACC TGGTGTGCGC GGACGTGGAC ATGGAGTTCC GCGACCACGT    420
```

```
GGGCGTGGAG ATCCTGACTC CACTGTTCGG CACCCTGCAC CCCGCCTTCT ACGGAAGCAG      480

CCGGGAGGCC TTCACCTACG AGCGCCGGCC CCAGTCCCAG GCCTACATCC CCAAGGACGA      540

GGGTGATTTC TACTACTTGG GGGGGTTCTT CGGAGGGTCG GTGCAGGAGG TGCAGCGGCT      600

CACCAGGGCC TGCCACCAGG CCATGATGGT CGACCAGGCC AACGGCATCG AGGCCGTGTG      660

GCACGACGAG AGCCACCTGA ACAAGTACCT GCTGCGCCAC AAACCCACCA AGGTGCTCTC      720

CCCCGAGTAC CTGTGGGACC AGCAGCTGCT GGGCTGGCCT GCGGTCCTGA GGAAGCTGAG      780

GTTCGCGGCG GTGCCCAAGA ACCACCAGGC GGTCCGTAAC CCGTGA                     826
```

(2) INFORMATION FOR SEQ ID NO: 4:

(i) SEQUENCE CHARACTERISTICS:
        (A) LENGTH: 826 base pairs
        (B) TYPE: nucleic acid
        (C) STRANDEDNESS: single
        (D) TOPOLOGY: linear (xi) SEQUENCE DESCRIPTION: SEQ ID NO: 4:

```
TAGGAAGGAC GTCCTTGTCG TGACCCCTTG GCTGGCTCCC ATTGTCTGGG AGGGCACGTT       60

CAACATCGAC ATCCTCAACG AGCAGTTCAG GCTCCAGAAC ACCACCATCG GGTTAACTGT      120

GTTTGCCATC AAAAAATACG TGGCCTTCCT GAAGCTGTTC CTGGAGACGG CGGAGAAGCA      180

CTTCATGGTG GGCCACCGCG TCCACTACTA CGTCTTCACC GACCAGCCGG CTGCGGTGCC      240

GCGCGTGGCG CTGGGGACCG GTCGGCAGCT GTCGGTGCTT GGGGTGCGCG CCTATAAGCG      300

CTGGCAGGAC GTGTCCATGC GCCGCATGGA GATGATCAGC GACTTCTGCG AGCGGCGCTT      360

CCTCAGCGAG GTGGATTACC TGGTGTGCGC GGACGTGGAC ATGGAGTTCC GCGACCACGT      420

GGGCGTGGAG ATCCTGACTC CACTGTTCGG CACCCTGCAC CCCGCCTTCT ACGGAAGCAG      480

CCGGGAGGCC TTCACCTACG AGCGCCGGCC CCAGTCCCAG GCCTACATCC CCAAGGACGA      540

GGGTGATTTC TACTACATGG GGGCGTTCTT CGGGGGGTCG GTGCAGGAGG TGCAGCGGCT      600

CACCAGGGCC TGCCACCAGG CCATGATGGT CGACCAGGCC AACGGCATCG AGGCCGTGTG      660

GCACGACGAG AGCCACCTGA ACAAGTACCT GCTGCGCCAC AAACCCACCA AGGTGCTCTC      720

CCCCGAGTAC CTGTGGGACC AGCAGCTGCT GGGCTGGCCT GCGGTCCTGA GGAAGCTGAG      780

GTTCACGGCG GTGCCCAAGA ACCACCAGGC GGTCCGGAAC CCGTGA                     826
```

(2) INFORMATION FOR SEQ ID NO: 5:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 5:

```
ACCGACCCCT CGAAGAACCC CCCCAA                                           26
```

(2) INFORMATION FOR SEQ ID NO: 6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO: 6:

```
GATGGTCTAC CCCCAGCCAA AGGTGCT                                          27
```

(2) INFORMATION FOR SEQ ID NO: 7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 7:

TGGGCCACCG TGTCCACTAC TATGTCTT                      28

(2) INFORMATION FOR SEQ ID NO: 8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO: 8:

CCAAGGACGA GGGTGATTTC T                            21

(2) INFORMATION FOR SEQ ID NO: 9:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 9:

TCCGGACCGC CTGGTGGTTC TTG                          23

(2) INFORMATION FOR SEQ ID NO: 10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 10:

AGCCCTCCCA GAGCCCCTGG                              20

(2) INFORMATION FOR SEQ ID NO: 11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO: 11:

TTGATGGCAA ACACAGTTAA CCCAATGG                      28

(2) INFORMATION FOR SEQ ID NO: 12:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO: 12:

AGAGGAGGCG GAAACTGAG                               19

(2) INFORMATION FOR SEQ ID NO: 13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 13:

TCTGAGCCTT CCAATGTCCG CTG        23

(2) INFORMATION FOR SEQ ID NO: 14:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO: 14:

GTCCACGCAC ACCAGGTAAT CCAC        24

(2) INFORMATION FOR SEQ ID NO: 15:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO: 15:

ACCCCCCCAA GTAGTA        16

(2) INFORMATION FOR SEQ ID NO: 16:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO: 16:

ACGCCCCCAT GTAG        14

(2) INFORMATION FOR SEQ ID NO: 17:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO: 17:

GGACGAGGGT GATTTCTACT ACT        23

(2) INFORMATION FOR SEQ ID NO: 18:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO: 18:

CAAGGACGAG GGTGATTTCT ACTACA        26

(2) INFORMATION FOR SEQ ID NO: 19:

```
        (i) SEQUENCE CHARACTERISTICS:
              (A) LENGTH: 25 base pairs
              (B) TYPE: nucleic acid
              (C) STRANDEDNESS: single
              (D) TOPOLOGY: linear (xi) SEQUENCE DESCRIPTION: SEQ ID NO: 19:

CGACCCCCCC GAAGAACGCC CCCAT                                              25

(2) INFORMATION FOR SEQ ID NO: 20:

(i) SEQUENCE CHARACTERISTICS:
              (A) LENGTH: 14 base pairs
              (B) TYPE: nucleic acid
              (C) STRANDEDNESS: single
              (D) TOPOLOGY: linear (xi) SEQUENCE DESCRIPTION: SEQ ID NO: 20:

TCCACGTCCA CGCA                                                          14

(2) INFORMATION FOR SEQ ID NO: 21:

(i) SEQUENCE CHARACTERISTICS:
              (A) LENGTH: 25 base pairs
              (B) TYPE: nucleic acid
              (C) STRANDEDNESS: single
              (D) TOPOLOGY: linear (xi) SEQUENCE DESCRIPTION: SEQ ID NO: 21:

CGCGGACGTG GACATGGAGT TCCGC                                              25

(2) INFORMATION FOR SEQ ID NO: 22:

(i) SEQUENCE CHARACTERISTICS:
              (A) LENGTH: 30 base pairs
              (B) TYPE: nucleic acid
              (C) STRANDEDNESS: single
              (D) TOPOLOGY: linear (xi) SEQUENCE DESCRIPTION: SEQ ID NO: 22:

GTGTGCGTGG ACGTGGACAT GGAGTTCCGT                                         30
```